United States Patent
Nash et al.

[11] Patent Number: 6,036,705
[45] Date of Patent: Mar. 14, 2000

[54] ANASTOMOSIS CONNECTION SYSTEM AND METHOD OF USE

[75] Inventors: John E. Nash, Chester Springs; Douglas G. Evans, Downingtown, both of Pa.

[73] Assignee: Kensey Nash Corporation, Exton, Pa.

[21] Appl. No.: 09/323,193

[22] Filed: Jun. 1, 1999

Related U.S. Application Data

[63] Continuation of application No. 08/861,584, May 22, 1997.

[51] Int. Cl.⁷ .................................................. A61B 17/00
[52] U.S. Cl. ............................................................. 606/153
[58] Field of Search ...................... 606/153, 151, 606/152, 191, 213, 155; 623/1, 12; 128/898, 899

[56] References Cited

U.S. PATENT DOCUMENTS

| | | |
|---|---|---|
| Re. 34,866 | 2/1995 | Kensey et al. . |
| 2,127,903 | 8/1938 | Bowen . |
| 3,155,095 | 11/1964 | Brown . |
| 3,570,013 | 3/1971 | Blumen . |
| 3,588,920 | 6/1971 | Wesolowski . |
| 3,620,218 | 11/1971 | Schmitt et al. . |
| 3,683,926 | 8/1972 | Suzuki . |
| 4,214,586 | 7/1980 | Mericle . |
| 4,233,981 | 11/1980 | Schomacher . |
| 4,352,358 | 10/1982 | Angelchik . |
| 4,366,819 | 1/1983 | Kaster . |
| 4,368,736 | 1/1983 | Kaster . |
| 4,470,415 | 9/1984 | Wozniak . |
| 4,501,263 | 2/1985 | Harbuck . |
| 4,512,761 | 4/1985 | Raible . |
| 4,523,592 | 6/1985 | Daniel . |
| 4,552,148 | 11/1985 | Hardy, Jr. et al. . |
| 4,553,542 | 11/1985 | Schenck et al. . |
| 4,657,019 | 4/1987 | Walsh et al. . |
| 4,675,008 | 6/1987 | Tretbar . |
| 4,712,551 | 12/1987 | Rayhanabad . |
| 4,721,109 | 1/1988 | Healey . |
| 4,744,364 | 5/1988 | Kensey . |
| 4,753,236 | 6/1988 | Healey . |
| 4,769,029 | 9/1988 | Patel . |
| 4,816,028 | 3/1989 | Kapadia et al. . |

(List continued on next page.)

FOREIGN PATENT DOCUMENTS

| | | |
|---|---|---|
| 154103 | 9/1985 | European Pat. Off. . |
| 688544 | 12/1995 | European Pat. Off. . |
| WO 88/06865 | 9/1988 | WIPO . |
| WO 93 02735 | 2/1993 | WIPO . |
| WO 96/25886 | 8/1996 | WIPO . |
| WO 97/40754 | 11/1997 | WIPO . |
| WO 97/43961 | 11/1997 | WIPO . |

OTHER PUBLICATIONS

Database WPI, Section PQ, Week 8710, Derwent Publications Ltd., London, GB Class P31, AN 97–070986, XP002074643 and SU 1243706A (Altai Poly).

*Primary Examiner*—Michael Buiz
*Assistant Examiner*—Vikki Trinh
*Attorney, Agent, or Firm*—Caesar, Rivise, Bernstein, Cohen & Pokotilow, Ltd.

[57] ABSTRACT

A system and method of use for effecting the bypass or other anastomosis of a portion of a native blood vessel, duct, lumen or other tubular organ within the body of a living being. The system includes an anastomosis connector device and a deployment instrument for carrying the device to the desired position within the vessel, duct, lumen or tubular organ. The deployment device may include a dilator to facilitate the placement of the anastomosis device within the interior of the vessel, duct, lumen or other tubular organ. The anastomosis device is preferably formed of a resorbable material and is configured to minimize blood or other fluid turbulence therethrough. The device may include snap-connectors or other components for securing it to the tissue of the vessel, duct, lumen or tubular organ and hemostasis-inducing sealing rings to prevent blood leakage. Other components may be included in the device for expediting the anastomosis procedure, with or without the use of sutures.

27 Claims, 11 Drawing Sheets

U.S. PATENT DOCUMENTS

| | | |
|---|---|---|
| 4,851,001 | 7/1989 | Taheri . |
| 4,852,568 | 8/1989 | Kensey . |
| 4,854,318 | 8/1989 | Solem et al. . |
| 4,930,502 | 6/1990 | Chen . |
| 4,931,057 | 6/1990 | Cummings et al. . |
| 4,957,499 | 9/1990 | Lipatov et al. . |
| 5,053,046 | 10/1991 | Janese . |
| 5,123,908 | 6/1992 | Chen . |
| 5,156,619 | 10/1992 | Ehrenheld . |
| 5,192,289 | 3/1993 | Jessen . |
| 5,222,963 | 6/1993 | Brinkerhoff et al. . |
| 5,250,058 | 10/1993 | Miller et al. . |
| 5,290,295 | 3/1994 | Querals et al. . |
| 5,304,195 | 4/1994 | Twyford, Jr. et al. . |
| 5,309,894 | 5/1994 | Heckele et al. . |
| 5,330,490 | 7/1994 | Wilk et al. . |
| 5,342,393 | 8/1994 | Stack . |
| 5,346,501 | 9/1994 | Regula et al. . |
| 5,364,389 | 11/1994 | Anderson . |
| 5,397,331 | 3/1995 | Himpens et al. . |
| 5,399,352 | 3/1995 | Hanson . |
| 5,411,520 | 5/1995 | Nash et al. . |
| 5,417,691 | 5/1995 | Hayhurst . |
| 5,425,738 | 6/1995 | Gustafson et al. . |
| 5,425,739 | 6/1995 | Jessen . |
| 5,443,497 | 8/1995 | Venbrux . |
| 5,445,644 | 8/1995 | Pietrafitta et al. . |
| 5,447,514 | 9/1995 | Gerry et al. . |
| 5,456,712 | 10/1995 | Maginot . |
| 5,456,714 | 10/1995 | Owen . |
| 5,503,635 | 4/1996 | Sauer et al. . |
| 5,509,902 | 4/1996 | Raulerson . |
| 5,545,178 | 8/1996 | Kensey et al. . |
| 5,549,617 | 8/1996 | Green et al. . |
| 5,571,167 | 11/1996 | Maginot . |
| 5,586,987 | 12/1996 | Fahy . |
| 5,591,226 | 1/1997 | Trerotola et al. . |
| 5,601,557 | 2/1997 | Hayhurst . |
| 5,649,959 | 7/1997 | Hannam et al. . |
| 5,655,548 | 8/1997 | Nelson et al. . |
| 5,676,670 | 10/1997 | Kim . |
| 5,695,504 | 12/1997 | Gifford, III et al. . |
| 5,709,335 | 1/1998 | Heck . |
| 5,766,220 | 6/1998 | Moenning . |
| 5,797,934 | 8/1998 | Rygaard . |
| 5,941,898 | 8/1999 | Moenning et al. ............ 606/213 |

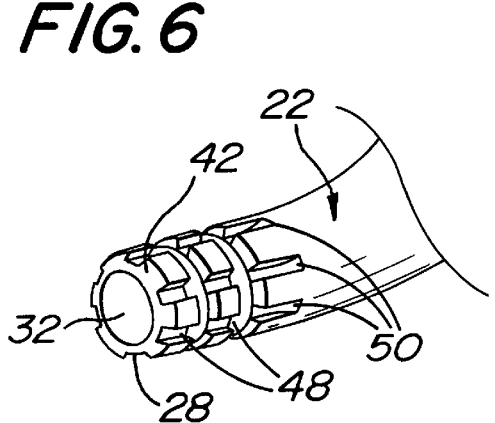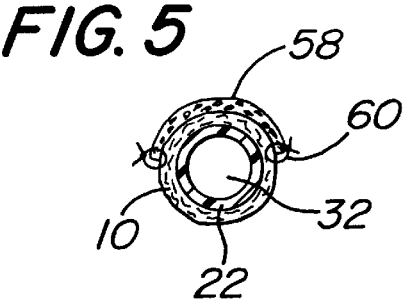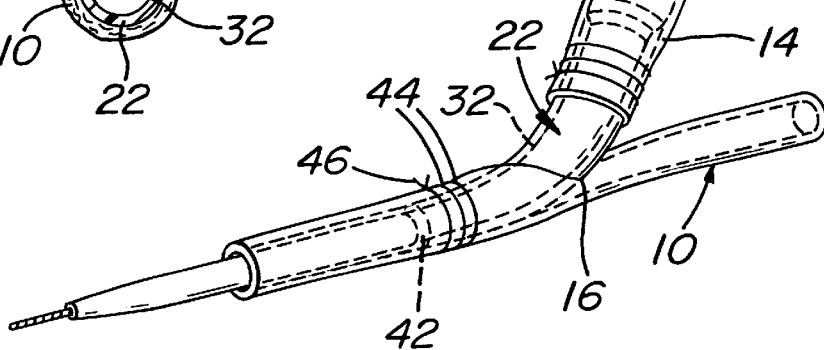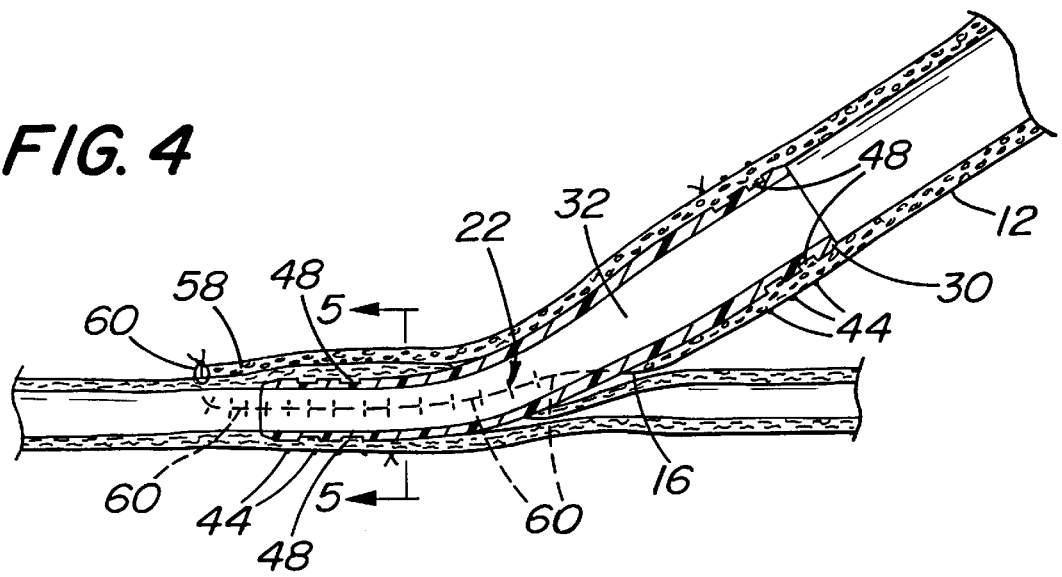

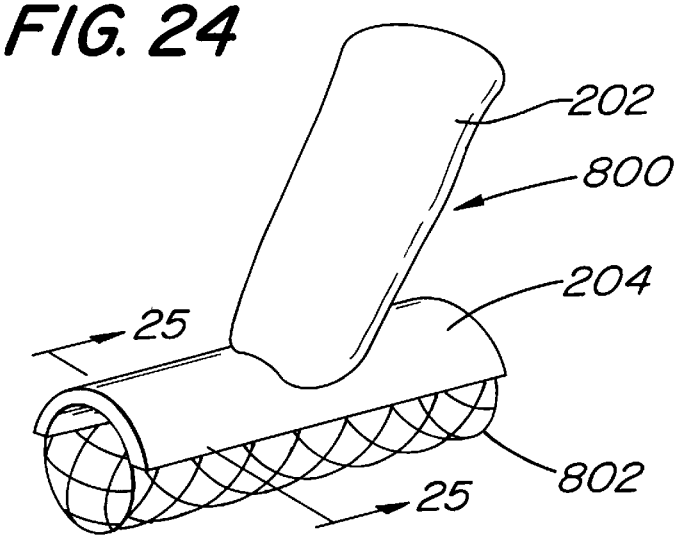
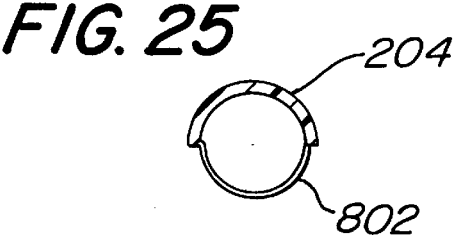
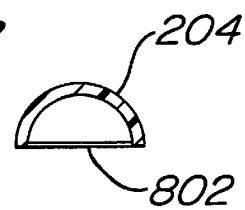
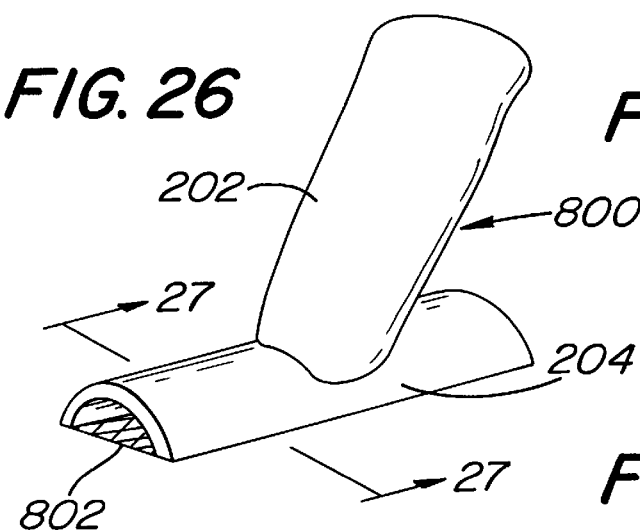
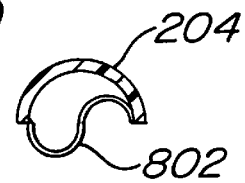
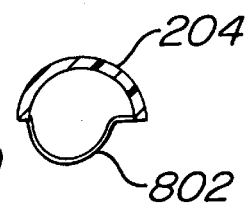

ANASTOMOSIS CONNECTION SYSTEM AND METHOD OF USE

RELATED APPLICATIONS

This application is a Continuation of our earlier filed U.S. patent application, Ser. No. 08/861,584, filed on May 22, 1997, entitled Anastomosis System and Method of Use, whose disclosure is incorporated by reference herein, and which is assigned to the same assignee as the subject invention.

BACKGROUND OF THE INVENTION

This invention relates generally to medical devices and methods of performing surgical procedures and more particularly to the anastomosis of blood vessels, ducts, lumens or other tubular organs.

Arterial bypass surgery is a common modality for the treatment of occlusive vascular disease. Such surgery typically involves a formal surgical incision and exposure of the occluded vessel followed by the joinder of a graft, e.g., a mammary artery, saphenous vein, or synthetic graft (all collectively referred to hereinafter as the "bypass graft"), to the occluded vessel (hereinafter the "native" blood vessel) distally (downstream) of the occlusion. The upstream or proximal end of the bypass graft is secured to a suitable blood vessel upstream of the occlusion, e.g., the aorta, to divert the flow of blood around the blockage. Other occluded or diseased blood vessels, such as the carotid artery, may be similarly treated. Moreover, similar procedures are conducted to place a graft between an artery and a vein in dialysis patients.

While such surgical procedures are widely practiced they have certain inherent operative limitations. For example, sewing the graft to the host vessel, known as anastomosis, requires complex and delicate surgical techniques to accomplish the optimum result. Various complications must be avoided when anastomosing a bypass graft, whether it be a natural graft or a synthetic graft. For example, it is important that the juncture between the native vessel and the bypass graft form a smooth uniform transition without narrowing or regional irregularities which could tend to reduce blood flow. Moreover, any protuberances into the lumen could obstruct blood flow and may produce turbulence, thereby increasing the risk of clotting and/or restenosis. In addition, the difference in size between the typically larger internal diameter of the bypass graft and the typically smaller native artery may also produce unwanted turbulence in the blood. All of these characteristics can greatly diminish the effectiveness and patency of the graft.

Various devices and methods of use have been disclosed for effecting anastomosis of blood or other vessels, ducts, lumens or other tubular organs. Examples of such devices and methods are found in U.S. Pat. No. 2,127,903 (Bowen), U.S. Pat. No. 3,155,095 (Brown), U.S. Pat. No. 3,588,920 (Wesolowski), U.S. Pat. No. 3,620,218 (Schmitt et al.), U.S. Pat. No. 3,683,926 (Suzuki), U.S. Pat. No. 4,214,586 (Mericle), U.S. Pat. No. 4,233,981 (Schomacher), U.S. Pat. No. 4,366,819 (Castor), U.S. Pat. No. 4,368,736 (Castor), U.S. Pat. No. 4,470,415 (Wozniak), U.S. Pat. No. 4,501,263 (Harbuck), U.S. Pat. No. 4,675,008 (Tretbar), U.S. Pat. No. 4,512,761 (Raible), U.S. Pat. No. 4,552,148 (Hardy, Jr. et al.), U.S. Pat. No. 4,721,109 (Healy), U.S. Pat. No. 4,753,236 (Healy), U.S. Pat. No. 4,769,029 (Patel), U.S. Pat. No. 4,851,001 (Taheri), U.S. Pat. No. 4,816,028 (Kapadia et al.), U.S. Pat. No. 4,854,318 (Solem et al.), U.S. Pat. No. 4,930,502 (Chen), U.S. Pat. No. 4,931,057 (Cummings et al.), U.S. Pat. No. 4,957,499 (Lipatov et al.), U.S. Pat. No. 5,156,619 (Ehrenfeld), U.S. Pat. No. 5,123,908 (Chen), U.S. Pat. No. 5,192,289 (Jessen), U.S. Pat. No. 5,250,058 (Miller), U.S. Pat. No. 5,222,963 (Brinkerhoff et al.), U.S. Pat. No. 5,330,490 (Wilk et al.), U.S. Pat. No. 5,346,501 (Regula et al.), U.S. Pat. No. 5,364,389 (Anderson), U.S. Pat. No. 5,399,352 (Hanson), U.S. Pat. No. 5,425,738 (Gustafson et al.), U.S. Pat. No. 5,425,739 (Jessen), U.S. Pat. No. 5,443,497 (Venbrux), U.S. Pat. No. 5,445,644 (Pietrafitta et al.), U.S. Pat. No. 5,447,514 (Jerry et al.), U.S. Pat. No. 5,456,712 (Maginot), U.S. Pat. No. 5,456,714 (Owen), U.S. Pat. No. 5,503,635 (Sauer et al.), U.S. Pat. No. 5,509,902 (Raulerson), U.S. Pat. No. 5,571,167 (Maginot), U.S. Pat. No. 5,586,987 (Fahy) and U.S. Pat. No. 5,591,226 (Trerotola et al.).

Notwithstanding the foregoing, a need still exists for systems and methods for effecting anastomosis which is quick, easy, effective and safe.

OBJECTS OF THE INVENTION

Accordingly, it is a general object of this invention to provide an anastomosis system and method of use which addresses that need.

It is a further object of this invention to provide a system and method of use for quickly, easily and safely effecting the anastomosis of vessels, ducts, lumens or other tubular organs.

It is a further object of the invention to provide absorbable devices for effecting the anastomosis of vessels, ducts, lumens, or other tubular organs.

It is a further object of this invention to provide an anastomotic coupling device for effecting the anastomosis of vessels, ducts, lumens or other tubular organs which is arranged for quick and sure placement with minimal chance of error.

It is a further object of this invention to provide a device for joining the ends of interrupted tubes or tubular organs of various sizes and functions, including, but not limited to, arteries, veins, lymphatic ducts, oviducts, ureters, intestines and the like.

It is a further object of this invention to provide an anastomotic coupling of particular utility for use in arterial bypass surgery which does not impede blood flow and which minimizes the blood turbulence which would normally result from a size differential between the two tubular bodies, e.g., the graft and the native blood vessel to which it is grafted.

It is a further object of this invention to provide an anastomotic fitting which provides a connection between a vascular bypass graft and the native blood vessel to which it is to be connected with a smooth uniform transition and which decreases in cross-sectional area in a controlled manner to reduce the possibility of blood turbulence therethrough.

It is a further object of the subject invention to provide a system for rapidly connecting two tubular bodies, e.g., a bypass graft to a native artery, without the need for sutures.

It is a further object of this invention to provide an anastomosis device for effecting the quick and easy anastomosis of two vessels, ducts, lumens or other tubular organs to each other while minimizing the chances for tissue necrosis.

It is a further object of this invention to provide an instrument system for effecting the quick and easy insertion of an anastomosis device into a vessel, duct, lumen or other tubular organ and for supporting a portion of the interior thereof during the anastomosis procedure.

SUMMARY OF THE INVENTION

These and other objects of the instant invention are achieved by providing a system for effecting the bypass or other anastomosis of a portion of a native blood vessel, duct, lumen or other tubular organ within the body of a living being with another vessel, duct, lumen, or other tubular organ, e.g., a bypass graft. The native blood vessel, duct, lumen or tubular organ has a wall with an opening provided therein. The system comprises an absorbable anastomosis device for connecting the graft to the native blood vessel, duct, lumen or tubular organ to establish a passageway for carrying fluid, e.g., blood, between the graft and the native vessel. A removable deployment instrument is provided. The removable deployment instrument is arranged for introducing at least a portion of the anastomosis device into the native vessel through the opening in the wall thereof and is arranged to be removed from the body of the being thereafter.

In accordance with one preferred aspect of the invention, the deployment instrument is arranged to dilate a portion of the native vessel contiguous with the opening to facilitate the introduction of at least a portion of the anastomosis device within the native vessel.

In accordance with another preferred aspect of this invention, the anastomosis device includes snap connection means for effecting the securement of the graft to the native vessel.

In accordance with another preferred aspect of the invention, the anastomosis device includes a passageway extending therethrough which decreases in cross-sectional area to provide a path for fluid, e.g., blood, to flow therethrough between the graft and the native vessel while minimizing turbulence therein.

In accordance with another preferred aspect of this invention, the system includes not only the anastomosis device and the removable deployment instrument but also an externally applied hemostasis-inducing means to establish a fluid resistant seal between the connected vessels and device.

DESCRIPTION OF THE DRAWING

Other objects and many of the attendant advantages of this invention will become readily appreciated as the same becomes better understood by reference to the following detailed description when considered in connection with the accompanying drawing wherein:

FIG. 3 is an isometric view of the system shown in FIG. 1, after the completion of an anastomosis of the bypass graft to the native artery and without requiring any suturing therebetween;

FIG. 4 is an enlarged side elevational view, partially in section, showing the system of FIG. 1, but utilizing an alternative bypass graft, i.e., one which is shaped and arranged to be sutured to the native artery after use of the anastomosis device of FIGS. 1–3;

FIG. 5 is a sectional view taken along line 5—5 of FIG. 4;

FIG. 6 is an isometric view of the distal end of the anastomosis device shown in FIG. 1;

FIG. 24 is an isometric view of still another alternative extendable anastomosis device of this invention for use for applications like that of FIGS. 19, 22 and 23, and wherein the device is shown in its fully extended or operative state;

FIG. 25 is a sectional view taken along line 25—25 of FIG. 24;

FIG. 26 is an isometric view similar to FIG. 24 but showing the device with its extendable component in an initial or retracted (compact) state;

FIG. 27 is a sectional view taken along line 27—27 of FIG. 26;

FIG. 28 is a sectional view, similar to FIG. 27 but showing an alternative extendable (evertable) member in its fully retracted (compact) state;

FIG. 29 is a view similar to FIG. 28 but showing the extendable member in an intermediate stage of its eversion;

FIG. 30 is a view, similar to that of FIG. 29 but showing the extendable member at a further stage of its eversion;

DETAILED DESCRIPTION OF PREFERRED EMBODIMENTS

Figure 1:
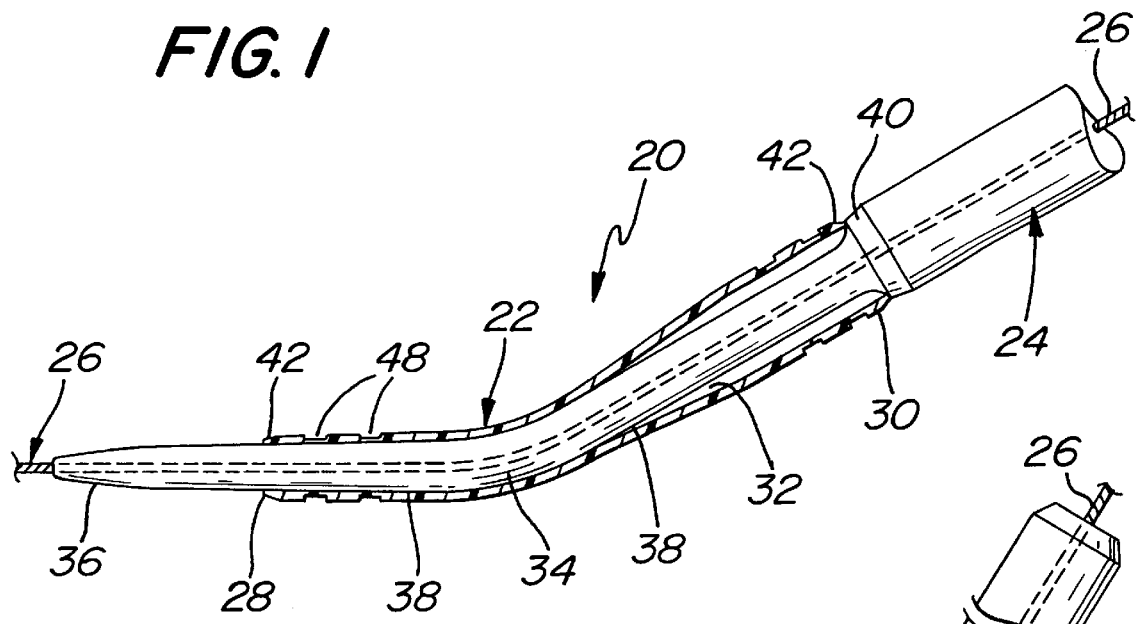
FIG. 1 is a side elevational view, partially in section, of one embodiment of an anastomosis system constructed in accordance with the subject invention, and showing one type of anastomosis device and the introducer instrument on which it is disposed for introduction into the body of a living being.

Referring now to the drawing wherein like reference characters refer to like parts, there is shown at 20 in FIG. 1 an anastomosis system constructed in accordance with the subject invention.

The system 20 basically comprises a resorbable anastomosis connector device 22 and a deployment instrument 24 for deploying the device 22. The deployment instrument 24 is arranged to be used in connection with a conventional, flexible guidewire 26. The anastomosis connector 22 and deployment device 24 are arranged to be used to effect the anastomosis of any two tubular organs, e.g., a native coronary artery 10 and a bypass graft 12 as shown in FIG. 3. In particular, the connector 22 is used to connect the distal end 14 of the bypass graft 12 to the native coronary artery 10 contiguous with an opening, puncture or incision 14 in the wall thereof. That opening may consist of a longitudinally extending slit, a transverse extending slit or any other suitably shaped opening extending through the wall of the vessel. That opening (e.g., an arteriotomy) can be made by any conventional means (e.g., a needle not shown).

It should be noted at this juncture that the anastomosis connector device 22 does not require the complete resection of the native artery 10 to place it. All that is required is the small opening 14 in the artery's wall. The proximal end of the bypass graft is arranged to be connected to any other suitable blood source, e.g., the aorta, via an anastomotic or natural connection thereto. For example, in the case where the mammary artery is used as the bypass graft its proximal connection to the aorta is left intact so that no anastomosis is needed to join it to the aorta. However, its resected distal end is connected to the anastomosis device 20.

It must be pointed out at this juncture that while the system 20 as described herein has particular utility for effecting coronary bypass surgery, the system is not limited to that application. In fact, the system is not limited to bypass surgery, but can be used for any anastomosis application to connect two or more vessels, ducts, lumens or tubular organs together.

As best shown in FIGS. 1 and 6 the anastomosis connector device 22 basically comprises an elongated tubular member formed of a resorbable, somewhat rigid, material, such as polyglactide, polyglycolide or copolymers thereof. The connector member 22 includes a distal end 28, a proximal end 30, and a central passageway 32 extending through the entire length of the connector 22 from its distal end to its proximal end. The passageway 30 is of circular cross-section and preferably tapers from its proximal end 30 toward its distal end 28. The taper may either be linear or non-linear, providing it is smooth and progressive in order to provide a smooth transition between the lumen of the bypass graft 12 and the lumen of the native vessel 10. This feature serves to reduce any turbulence in the blood flowing from the bypass graft 12 (which is commonly of larger internal diameter than the internal diameter of the native vessel) to the native vessel.

While the anastomosis device is preferably formed of a resorbable material, such as that described above, for some applications it need not be resorbable.

In order to connect the bypass graft to the native artery, the anastomosis connector 22 is arranged to be located partially within the native artery and partially within the bypass graft. The connector 22 serves to support the associated portions of the native artery and bypass graft during the anastomosis procedure, thereby facilitating that procedure. Moreover, owing to the construction of the connector 22, it can be used to effect the anastomosis between the native artery and the graft without the need for any surgical suturing, although such suturing can be used to enhance the securement of the anastomosis. In any case, once the anastomosis has been completed, blood will be enabled to flow from the bypass graft into the native vessel. By making the anastomosis device of a resorbable material so that the body will absorb it over time, it will not remain within the interior of the anastomosed vessels after absorption. Thus, once absorbed it cannot present any health hazard or risk inherent with other permanent intravascularly placed non-resorbable devices, e.g., stents, etc.

As can be seen in FIG. 1, the anastomosis connector 22 is not linear, but rather it includes a slightly arcuate intermediate portion between generally linear proximal and distal ends. In particular, the portion of the connector contiguous with the proximal end 30 is linear as is the portion contiguous with the distal end. The intermediate portion is slightly arcuate, whereupon the longitudinal central axis of the linear proximal portion extends at an acute angle to the longitudinal central axis at the linear distal portion. The angled configuration of the connector device 22 facilitates its insertion into the native vessel (as will be described later).

The anastomosis connector is initially disposed on the deployment instrument 24 so that it can be carried to its operative situs partially within the interior lumen of the native vessel 10. To that end, as can be seen in FIG. 1, the deployment device 24 basically comprises an elongated flexible member whose distal end portion 34 is arranged to support the anastomosis connector 22 thereon. The instrument 24 includes a central lumen through which the guidewire 26 passes. The free end of the instrument serves as a dilator and hence includes a tapered leading surface 36 which merges into a cylindrical surface 38 of circular cross section. The proximal end of the surface 38 terminates in a shoulder or a wall 40 of larger outside diameter than the diameter of the surface portion 38 and of larger diameter than the passageway 32 at the proximal end of the anastomosis connector 22.

Figure 2:
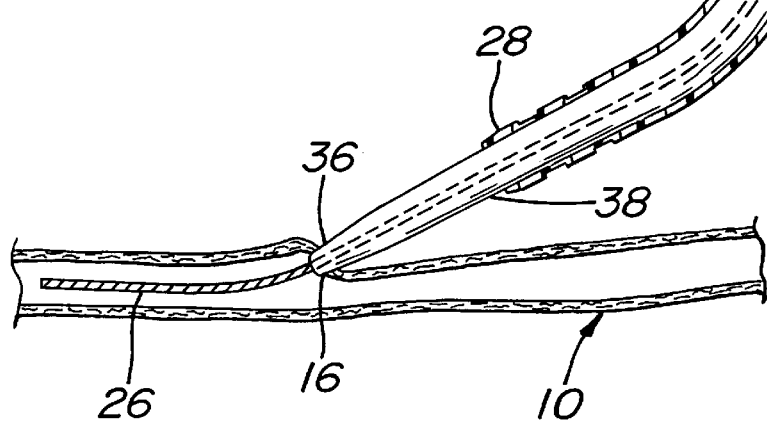
FIG. 2 is a slightly reduced side elevational view, partially in section, showing the system of FIG. 1 during an initial step in the procedure of placing the anastomosis device through an incision or puncture in a native blood vessel, e.g., a coronary artery, without requiring the complete resection of the native vessel to place the anastomosis device.

The outer diameter of the surface portion 38 proximally of its tapered dilator tip 36 is approximately the same diameter as the inside diameter of the passageway 32 of the anastomosis device 22 at the distal end thereof so that the anastomosis device can be seated on the deployment instrument with its proximal end 30 abutting the shoulder or stop 40. Since the outside diameter of the portion 38 of the deployment instrument is approximately equal to the inside diameter of the passageway 32 at the distal end of the anastomosis connector 22, the connector will stay in place in position like shown in FIG. 1 to facilitate its introduction into the interior of the native vessel 10. To that end the instrument 24 with the anastomosis connector 22 thereon is arranged to be threaded over the guidewire 26 (the guidewire having previously been positioned so that it extends into the opening 16 in the native blood vessel 10 as shown in FIG. 2) until its dilator end 36 contacts the tissue of the native blood vessel contiguous with the opening 16.

The deployment instrument is then slid further down the guidewire 26 until its tapered distal end 36 enters into the small opening 16 in the native vessel 10. Further insertion of the deployment instrument along the guidewire causes the dilator's tapered surface to dilate or stretch the tissue of the native vessel contiguous with the opening 10 to a point sufficient to enable the distal end 28 of the anastomosis connector 22 to pass therethrough, whereupon the distal end of the anastomosis device is located distally, that is downstream of the opening in the native vessel. In order to facilitate the introduction of the anastomosis connector 22 into the native vessel its leading or forward edge of the distal end 28 is chamfered at 42. The proximal end of the anastomosis connector extends out of the opening 16 in the native artery to serve as the means for connection to the bypass graft (as will be described later).

As shown clearly in FIG. 3 the distal end of the anastomosis device is secured in its desired position within the native artery 10 by use of plural lashes or loops 44, e.g., suture material, extended about the circumference thereof at the distal end and tied in place by a knot 46. In order to hold the lashes or loops of suture in place so that they will not slide, the distal end of the anastomosis device includes a pair of annular recesses 48 in its outer surface. The recesses are adapted to receive contiguous portions of the native artery forced therein by the lashes which are drawn thereabout. In order to minimize the chance of the interposed vascular tissue becoming necrotic due to the pressure applied by the lashes a plurality of longitudinally oriented, pressure reducing recesses or slots 50 are preferably provided in the outer surface of distal end of the anastomosis connector as shown in FIG. 6. The recesses 50 provide areas of reduced pressure on the tissue of the native vessel contiguous with the encircling lashes 44. Alternatively, a plurality of raised ridges can be provided extending along the distal end of the anastomosis connector to create the areas of reduced pressure therebetween.

The bypass graft 12 is arranged to be threaded through all or at least a portion of the proximal end of the deployment instrument 24 so that the open distal end 14 of the graft 12 can be located and disposed over the proximal end 30 of the anastomosis connector 22 which extends out of the opening 16 in the native vessel 10.

If the surgeon conducting the anastomosis wishes, the bypass graft 12 may include an opening or slot 52 through its wall proximally of the free distal end 14 and through which the proximal end of the delivery system instrument 24 can be extended as shown in FIG. 3. This arrangement enables the proximal end 18 of the bypass graft 12 to be presecured to the upstream blood vessel site, e.g., the aorta. In particular, with this arrangement, the proximal end 18 of the bypass graft can be connected first before connecting its distal end 14 to the anastomosis connector 22 and the native artery. This approach appears preferable when the bypass graft is the mammary artery whose natural proximal connection to the aorta is to be maintained. If, however, the distal end of the bypass graft is to be connected first, or if threading the entire instrument 24 through the entire length of the bypass graft isn't objectionable, then no side opening in the wall of the bypass graft needs to be made. Instead, the delivery system instrument 24 can be extended fully through the bypass graft 12 as shown by the phantom lines in FIG. 3. The free (distal) end 14 of the bypass graft 12 is then slid over the proximal end of the anastomosis connector 22. The proximal end of the connector 22 is also chamfered at 42 to facilitate its introduction into the open distal end 14 of the bypass graft 12.

A plurality of lashes in the form of suture loops 44, like that described at the proximal end of the anastomosis connector are then extended about the distal end 14 of the bypass graft 12 where it receives the proximal end of the anastomosis device. In order to hold the anastomosis connector securely in place within the bypass graft, the proximal end of the anastomosis connector also includes the pair of annular recesses 48 and the longitudinally extending pressure-reducing recesses 50 in the distal end thereof.

As mentioned earlier, the slit or opening 16 provided in the native vessel can be either transverse, or any other shape. Since axial opening or slit has the potential for splitting longitudinally when dilated by the deployment instrument, a small transverse slit may be desirable.

When anastomosis connector 22 is in place as just described, it serves to support the native artery distally of the opening therein to prevent the collapse thereof while also supporting the distal end of the bypass graft during the anastomosis procedure, thereby facilitating that procedure. Once the anastomosis device is secured in place, e.g., the lashes or loops 44 applied, the deployment instrument 24 system's can be removed by sliding it out along the guidewire. Then the guidewire can be removed, leaving the anastomosis connector in place with both the native artery and the bypass graft secured thereto, whereupon blood can freely flow from the interior of the bypass graft through the anastomosis connector's passageway 32 and into the native artery. The smooth tapered passageway 32 ensures that the flow of blood from the larger diameter bypass graft into the smaller diameter native artery will be relatively non-turbulent.

As should be appreciated by those skilled in the art, with the anastomosis connector 22 in place any blood flow through the native artery proximally of the anastomosis (to the extent that it existed before) will be halted by the interposed wall of the anastomosis connector. If it is desired to have some blood flow from the portion of native artery proximally of the anastomosis, (e.g., if that portion of the artery is not totally occluded so that blood can still flow therethrough), then the anastomosis device 22 may be provided with one or more openings (not shown) in its side wall to communicate with the interior of the proximally located portion of the native artery to allow whatever blood flow is flowing therethrough to enter that opening in the wall of the anastomosis connector and merge with the blood flowing from the bypass graft.

Figure 11:
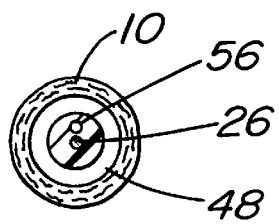
FIG. 11 is a sectional view taken along line 11—11 of FIG. 10.
Figure 10:
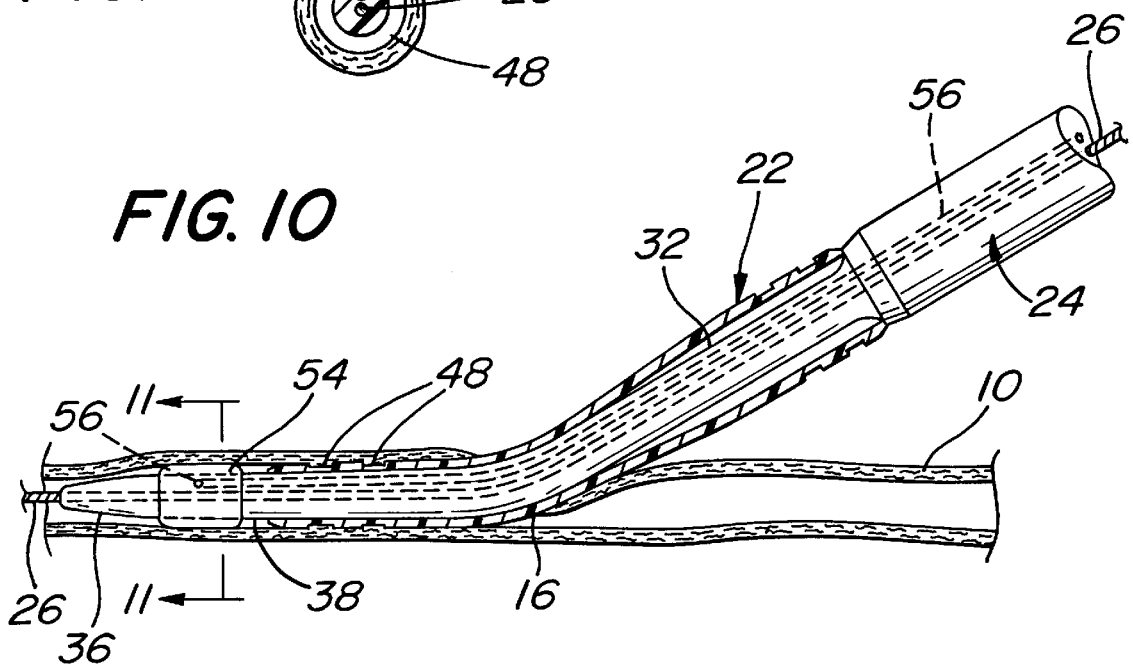
FIG. 10 is a side elevational view, partially in section, showing the anastomosis device of FIG. 1 in the process of being deployed by an alternative deployment instrument, e.g., an inflatable dilator, constructed in accordance with this invention.

For some applications it may be desirable to provide additional dilation of the interior of the native artery distally of the opening 16 than can be effected by a fixed size tapered wall dilator 36 like that shown in FIG. 2. In such a case, the deployment instrument 24 may also include an expandable annular balloon to serve as an additional dilator located distally of the tapered end fixed dilator 36. This alternative embodiment of the instrument 24 is shown in FIG. 10. In particular, as can be seen therein, the deployment instrument 24 includes an annular inflatable balloon 54 located slightly proximately of the tapered distal end 36 of the instrument 24. The balloon includes a hollow interior which is in communication with a lumen 56 extending longitudinally through the deployment instrument 24. This lumen serves to inflate the balloon to expand it outward radially so as to dilate the tissue of the native blood vessel contiguous therewith as shown in FIGS. 10 and 11. This action may facilitate the introduction of the distal end of the anastomosis connector 22 into its desired operative position within the native vessel as shown in FIG. 10. The lumen 56 also serves to deflate the balloon 54 when it is desired to remove the deployment instrument 24.

In FIGS. 4 and 5 there is shown an alternative manner of effecting the anastomosis with the anastomosis connector 22. In this alternative methodology the bypass graft 12 is surgically contoured or shaped so that its distal end is not a straight transverse cut like that shown heretofore. Instead the free or distal end of the bypass graft is cut or otherwise shaped to form an elongated tongue or flap. This tongue or flap 58 can then be disposed over and slightly surrounding the contiguous surface of the native artery to be sutured thereto and about the opening 16 via a line of plural sutures 60 as shown in FIGS. 4 and 5. Such suturing has the benefit of providing additional direct securement between the tissue of the bypass graft 12 and the tissue of the native artery 10. Moreover, blood loss through the interface at the site of the anastomosis can be reduced by this securement technique.

Figure 7:
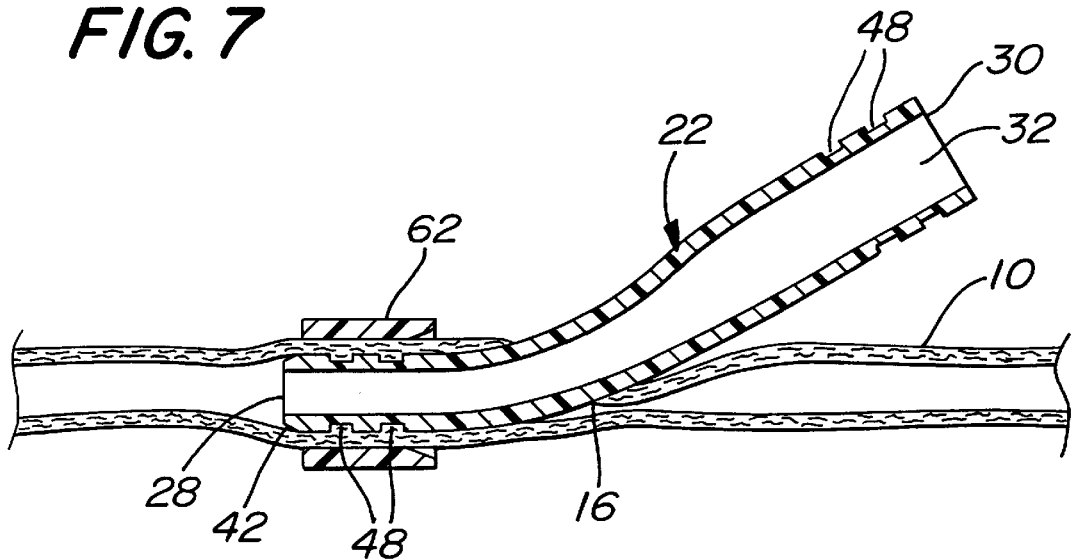
FIG. 7 is a longitudinal sectional view showing a portion of the anastomosis device of FIG. 1, but with alternative means utilized to secure its distal end to the native vessel.

In FIG. 7 there is shown an alternative embodiment of means for securing the anastomosis connector 22 to its associated vessel or graft. In the embodiment shown in FIG. 7 the securement means is in the form of a locking ring designated by the reference number 62. This ring serves as a replacement for the suture loops or lashes 44. Preferably the ring is split and formed of a rigid, yet somewhat flexible resorbable material so that it can be opened at its split to enable it to be extended around the distal end of the anastomosis connector 22 once the connector is in place within the native artery. The locking ring, being flexible, will snap back in place so that its central passageway tightly encircles the tissue of the native artery between it and the pair of annular recesses 48 in the anastomosis connector to hold the connector securely in place. The bypass graft 12 can be connected to the proximal end of the anastomosis device 22 in the same manner.

Figure 8:
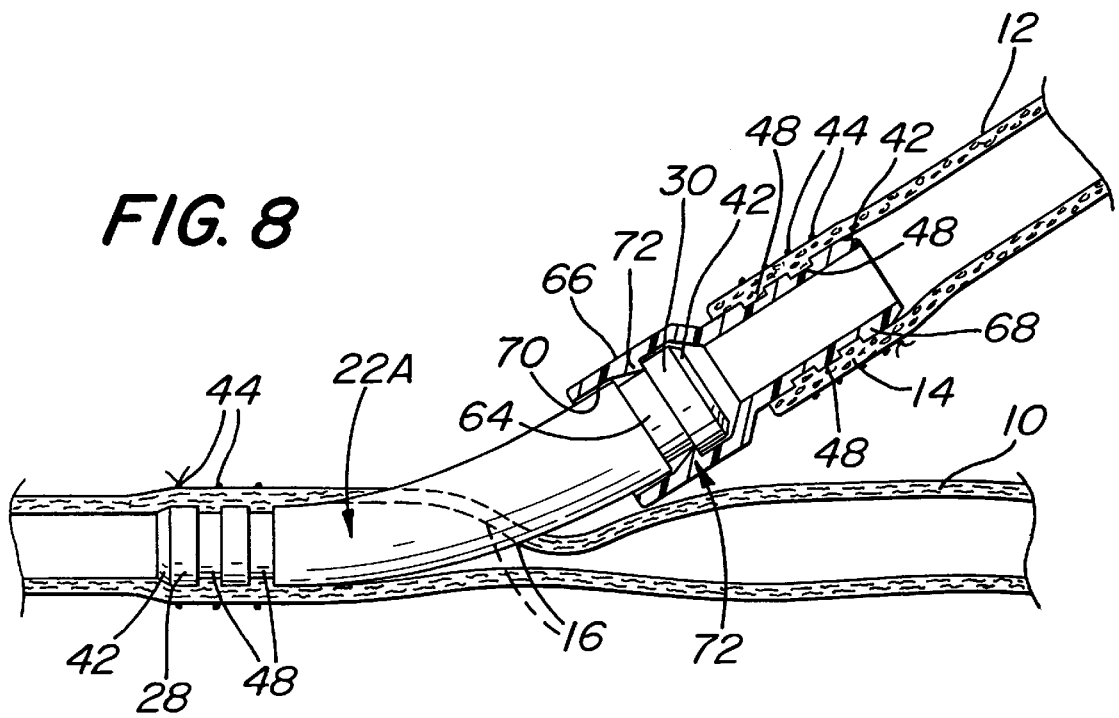
FIG. 8 is a side elevational view, partially in section, showing an alternative embodiment of an anastomosis device in place within a native vessel and to which the distal end of a bypass graft is snap-connected thereto.

In FIG. 8 there is shown an alternative embodiment 20A to the anastomosis connector 20 described heretofore. The anastomosis connector 22A is identical in many respects to connector 22 so the common features will be given the same reference numbers and the construction and operation of such common features will not be reiterated in the interests of brevity. Thus, as can be seen the connector 22A basically comprises a hollow tubular member whose proximal end 30 includes a single locking annular recess 64 extending thereabout. This recess is arranged to be connected to a mating coupling 66 which is fixedly secured to the distal end 14 of the bypass graft 12. The coupling 66 basically comprises a tubular member, formed of the same material as the anastomosis device 22 and has a cylindrical proximal end 68. The proximal end includes a pair of annular recesses 48 like those described heretofore. This portion of the connector is arranged to be disposed within the open distal end 14 of the bypass graft 12. The proximal end surface of the coupling 66 is chamfered at 42 to facilitate placement within the bypass graft. The proximal end of the coupling 66 is arranged to be secured in place to the bypass graft via plural lashes 44 wrapped thereabout in the same manner as described earlier.

The distal end of the coupling 66 is in the form of a hollow socket 70 whose inside diameter is just slightly larger than the outside diameter of the proximal end 30 of the anastomosis connector 22. A plural of ramp-like, inclined detents 72 extend about the inner periphery of the hollow socket 70 for receipt within the annular groove 64 in the proximal end of the anastomosis connector 22. Accordingly, the proximal end of the anastomosis connector can be inserted into the hollow socket of the coupling 66, whereupon the detents snap-fit into the annular groove 64, thereby securing the distal end of the bypass graft to the anastomosis connector 22. Since the distal end of the anastomosis connector is fixedly secured within the native artery 10 distally of the opening 16, once the snap connection between the anastomosis connector 22 and the coupling 66 has been effected, the anastomosis is complete. No suturing of tissue is necessary.

Figure 9:
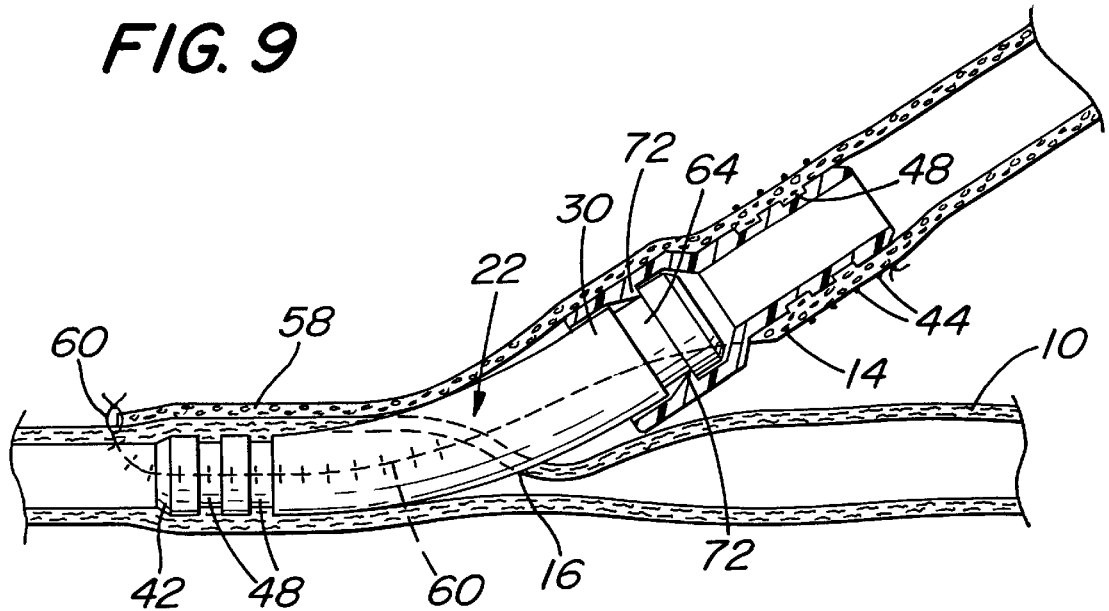
FIG. 9 is a view similar to FIG. 4 but showing the alternative anastomosis device of FIG. 8 using the specially shaped bypass graft of FIG. 4 to enable the graft to be sutured to the native blood vessel.

In the event that the surgeon wishes to make use of sutures to provide some additional securement between the vascular tissue, the distal end of the bypass graft can be formed into the extending tongue like that described earlier and the tongue disposed over the contiguous portions of the native artery and secured thereto by plural sutures as shown in FIG. 9.

Figure 12:
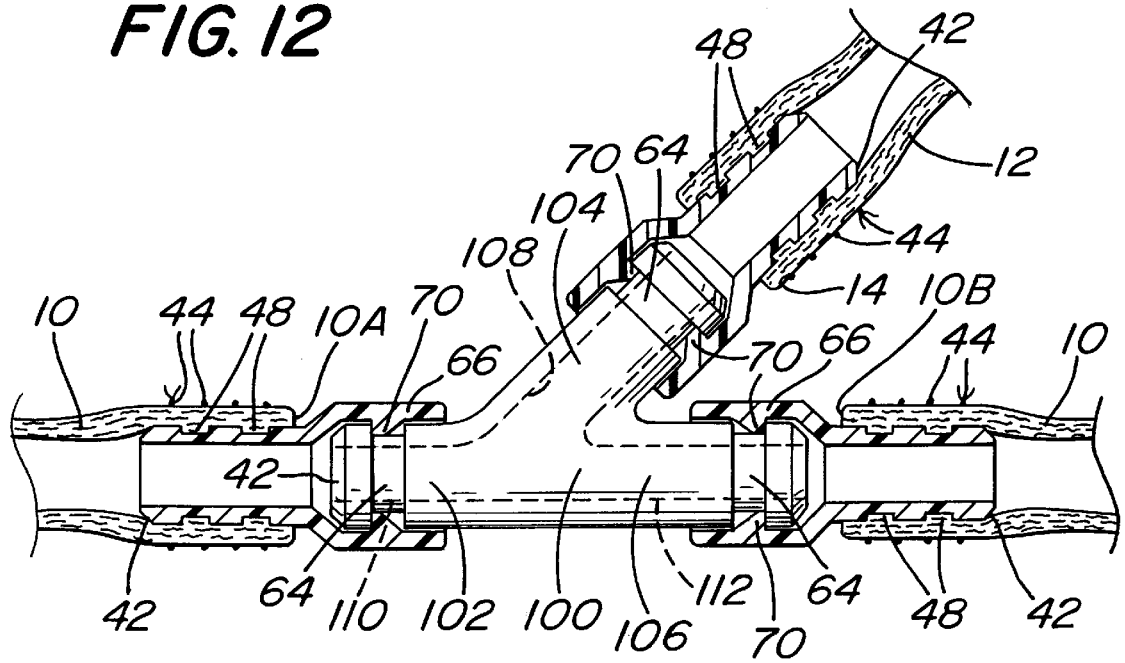
FIG. 12 is a side elevational view, partially in section, of an alternative embodiment of an anastomosis device constructed in accordance with this invention which requires the complete resection of the native vessel for placement therein, and which when placed, enables blood to flow through the bypass graft and through the native vessel upstream of the junction (to the extent that the upstream portion of the native vessel can carry any blood therethrough)

In FIG. 12 there is shown yet another alternative embodiment of an anastomosis connector 100 constructed in accordance with this invention. The connector 100 basically comprises a central or branched connector for connection between an adjacent pair of completely resected ends 10A and 102 of the native vessel 10 and the distal end 14 of the bypass graft 12. To that end the branched connector member 100 is arranged to be connected to three couplings 66, each of which is connected to a respective end of the native vessel or bypass graft, as the case may be. The branched member 100 includes a tubular distal end portion 102, a tubular proximal end portion 104 and a tubular intermediate end portion 106. All of the tubular end portions are in communication with one another via respective passageways extending therethrough. While not shown in the interest of drawing simplicity the passageway 108 in the proximal end portion 104, preferably tapers in cross-section in controlled manner like that described heretofore to result in the reduction of the blood turbulence therethrough. The passageways 110 and 112 in the distal end portion 102 and intermediate end portions 106, respectively, are of the same uniform size and are axially aligned. Each of the couplings 66 is constructed identically to the coupling 66 described earlier and will not be described further in the interests of brevity.

The central branched connector 100 is connected between the resected ends 10A and 10B of the native vessel, e.g., artery, 10. One coupling 66 is mounted on the native vessel section contiguous with the end 10A in the same manner as described earlier with respect to the mounting of the coupling 66 on the bypass graft 12. Another coupling 66 is similarly mounted on the native vessel section contiguous with end 10B. The third coupling 66 is mounted on the distal end 12 of the bypass graft 12 in the same manner as described earlier.

The proximal end portion 104 of the central branched connector 100 is arranged to be snap-fit connected to the coupling 66 on the bypass graft in the same manner as described with reference to FIG. 8. Thus, the portion 104 includes the heretofore described annular recess 64 for receipt of the detents 70 of the coupling 66. The trailing end portion 10A of the native artery is connected to the distal end portion 102 of the central branched connector by snap-fitting the detents 70 of its coupling 66 onto the annular recess 64 in the end portion 102 of the connector 100. In a similar manner the leading end 10B of the native vessel 10 is connected to the intermediate end 106 of the branched connector 100 via the snap-fitting of its coupling's detents 70 onto the annular recess 60 of the immediate end portion 106.

Figure 13:
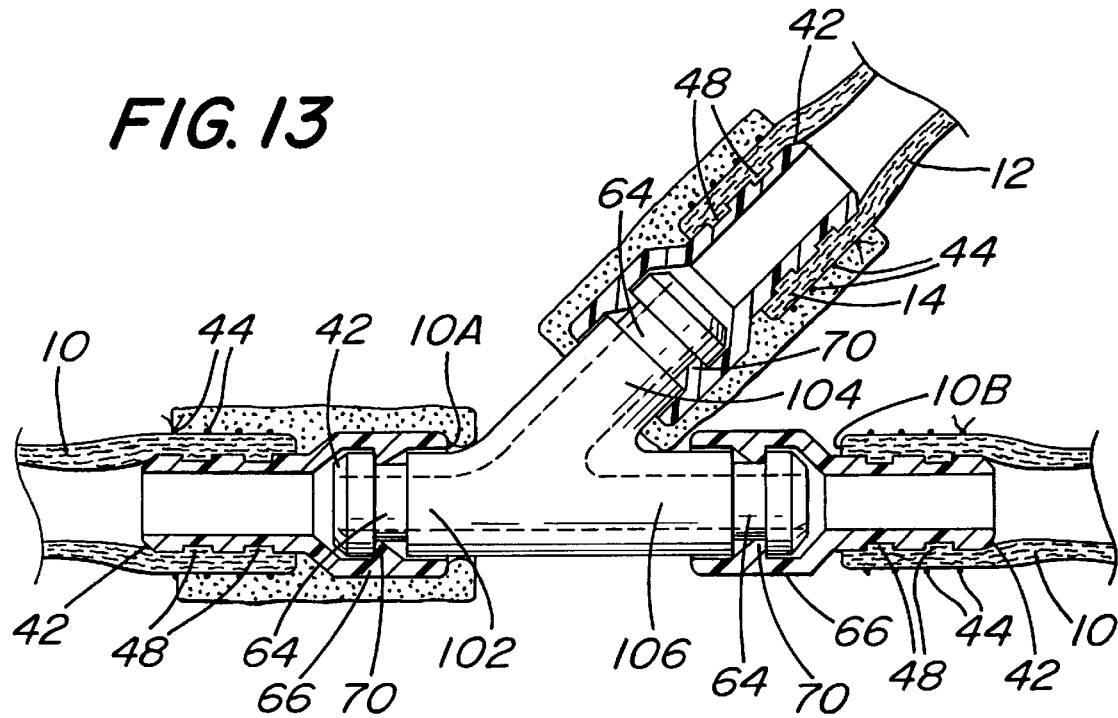
FIG. 13 is a view similar to that of FIG. 12 but showing the use of hemostasis inducing sleeve members forming a part of the system of this invention to promote hemostasis at the anastomosis connection sites.

In order to reduce bleeding at the situs of each connected coupling 66 to its associated vessel and to the anastomosis connector 100, a plurality of hemostasis-inducing sleeves can be provided. In the embodiment shown in FIG. 13 two such sleeves 114 are shown, one disposed about the end 10A of the native artery and the other disposed about the end 14 of the bypass graft. Each sleeve is preferably formed of collagen. If desired a third sleeve 114 may be placed about the end 10B of the native artery 10.

Figure 14:
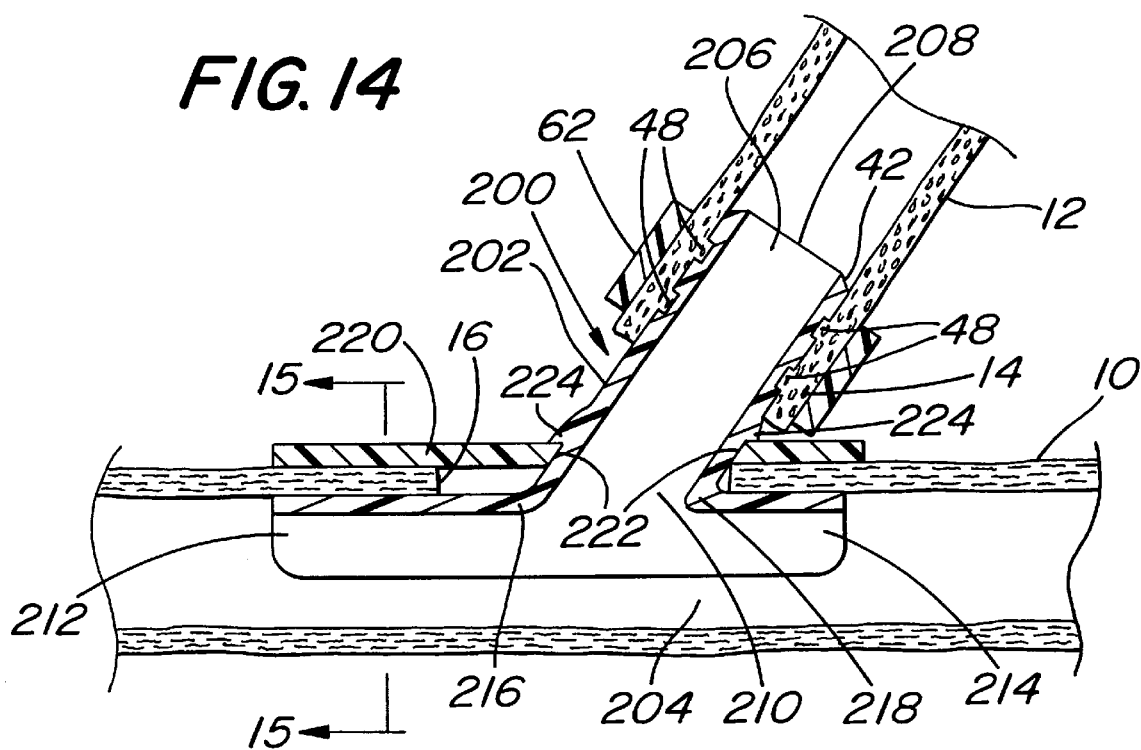
FIG. 14 is a sectional view of an alternative anastomosis device constructed in accordance with the subject invention and which can be used in applications to enable blood to flow through the upstream portion of the native vessel like that shown in FIGS. 12 and 13, but which does not require the complete resection of the native vessel as does the anastomosis device of FIGS. 12 and 13.

In FIG. 14 there is shown another embodiment of an anastomosis connector device 200 constructed in accordance with this invention. The connector 200 is arranged to be inserted through a short slit or other opening 16 in the wall of the native vessel 10. The length of the slit in the longitudinal direction should be sufficiently long to enable the introduction of the anastomosis connector 200 therein, as will be described hereinafter. Unlike the connector 100, the connector 200 does not require complete resection of the native vessel 10 in order to be used.

The connector 200 basically comprises a tubular proximal portion 202 and a culvert or trough-shaped member 204 located on the distal end of the tubular portion 202. The tubular portion 202 is constructed similarly to the proximal portion 104 of the connector 100 and includes a passageway 206 extending therethrough from its proximal end 208 to its distal end 210 (that is, the end which merges with the culvert shaped member 204). The passageway 206 tapers from the proximal end to the distal end in a controlled manner as described earlier (although this isn't shown in FIG. 14 in the interest of drawing simplicity). The proximal end of the tubular portion 202 is chamfered at 42 and includes a pair of recesses 48 extending around its periphery as described heretofore.

The culvert-shaped member 204 is preferably of an arcuate shape having a front end portion 212 extending distally of the distal side of the tubular portion 202 and a rear or intermediate portion 214 extending in the opposite direction from the front portion 212. The front or distal portion 212 is arranged to be inserted through the opening or slit 16 in the native vessel 10 and slid forward until the leading edge of the opening or slit abuts the tubular portion 202 where it merges with the culvert-shaped member 204. This merger point is designated by the reference number 216. The length of the culvert member 204 from the merger point 216 to the edge of rear portion 214 is selected to be approximately equal to the length of the opening or slit 16 measured in the longitudinal direction. Thus, the front or distal edge of the culvert portion 212 can be introduced through the slit 16 and slid forward until the leading (distal) edge of the slit 16 abuts the merger point 216, whereupon the anastomosis connector 200 can be rotated downward or inward to cause the rear edge of culvert portion 214 to pass through the slit 16 until the connector is oriented such that the longitudinal axis of its culvert member 204 is parallel to the longitudinal axis of its native vessel 10. The anastomosis device can then be retracted or pulled proximally within the native vessel 10 so that the point 218 at which the rear portion 214 of the culvert member 204 merges with the tubular portion 202 abuts the trailing end of the slit 16 as shown in FIG. 14. In this position part of the front portion 212 of the culvert member 204 will underlie a portion of the native vessel 10 contiguous with the leading edge of the slit 16 and the rear portion 214 of the culvert member 204 will underlie the native vessel contiguous with the trailing edge of that slit, thereby preventing the anastomosis connector 200 from being pulled out of the native vessel.

In order to further lock the anastomosis connector 200 in place in the native vessel, with the tubular portion 202 extending out of the slit 16, a locking plate 220 is provided as part of the connector 200. The plate 220 is of a general culvert-shape and comprises a curved wall (see FIG. 15) whose inside diameter is similar to the outside diameter of the native vessel so that it can engage a substantial portion, e.g., 120°, of the periphery of the native vessel. The locking plate 220 includes a passageway 222 extending therethrough. The passageway 222 is of the diameter of the tubular portion 202 of the connector 200 and extends at an acute angle to the longitudinal axis of the locking plate as shown in FIG. 14. This angle is the same as the angle that the longitudinal axis of the tubular portion 202 of the connector extends to the longitudinal axis of the culvert-shaped member 204. Thus, the tubular portion 202 of the connector can be extended through the passageway 222 in the locking plate 220. In order to hold the locking plate 220 in place with the portions of the native artery contiguous with the slit 16 interposed between it and the interiorly located culvert-shaped member 204, the tubular portion 202 of the connector includes plural inclined detents 224. The detents 224 are each inclined or ramp-like members and are disposed at spaced locations about the periphery of the tubular portion 202.

Figure 15:
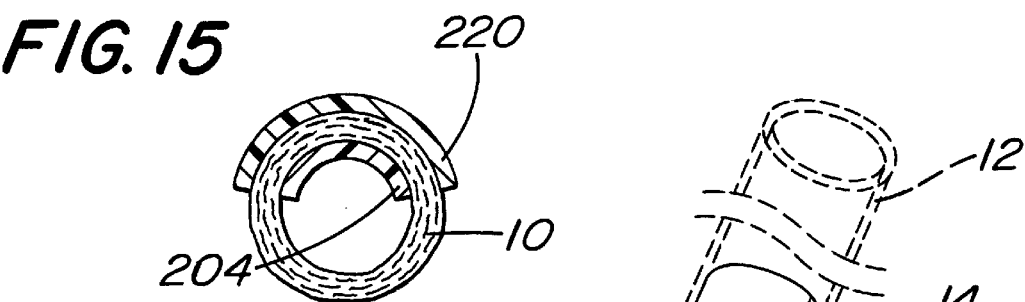
FIG. 15 is a sectional view taken along line 15—15 of FIG. 14.

Use of the anastomosis connector 200 of FIGS. 14 and 15 is as follows. The anastomosis connector 200, without the locking plate 220 and free of any connection to the bypass graft 12, is inserted into the interior of the native vessel in the manner as described earlier so that the tubular portion extends out through the slit 16 in the wall of the native vessel. The locking plate 220 is then slid over the chamfered distal end 42 of the tubular portion 202 of the connector 200 and down over the inclined surfaces of the detents 224 until it snap-locks in place thereunder as shown in FIG. 14. In this state the wall of the native vessel 10 contiguous with the slit 116 and extending about the tubular portion 202, will be locked between the locking plate 220 and the interiorly located culvert-shaped member 204. The open distal end 14 of the bypass graft 12 can then be slid down over the chamfered proximal end 208 of the anastomosis device to the position shown in FIG. 14. At this point a split locking ring 62 like that described heretofore can be disposed about the distal end of the bypass graft to secure it in place. Alternatively, plural loops or lashes 44 can be disposed about the distal end of the bypass graft to secure the bypass graft to the anastomosis connector 200.

Figure 16:
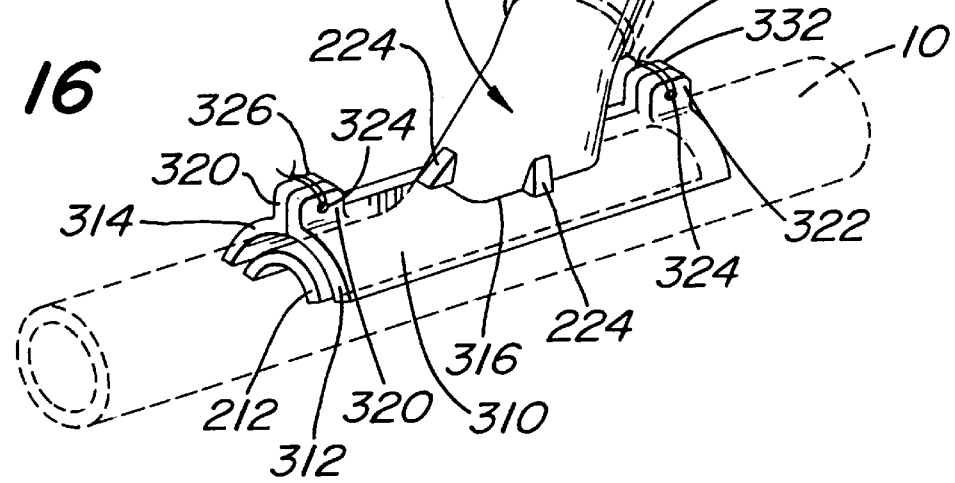
FIG. 16 is an isometric view showing an alternative embodiment of the anastomosis device of FIGS. 14 and 15.
Figure 17:
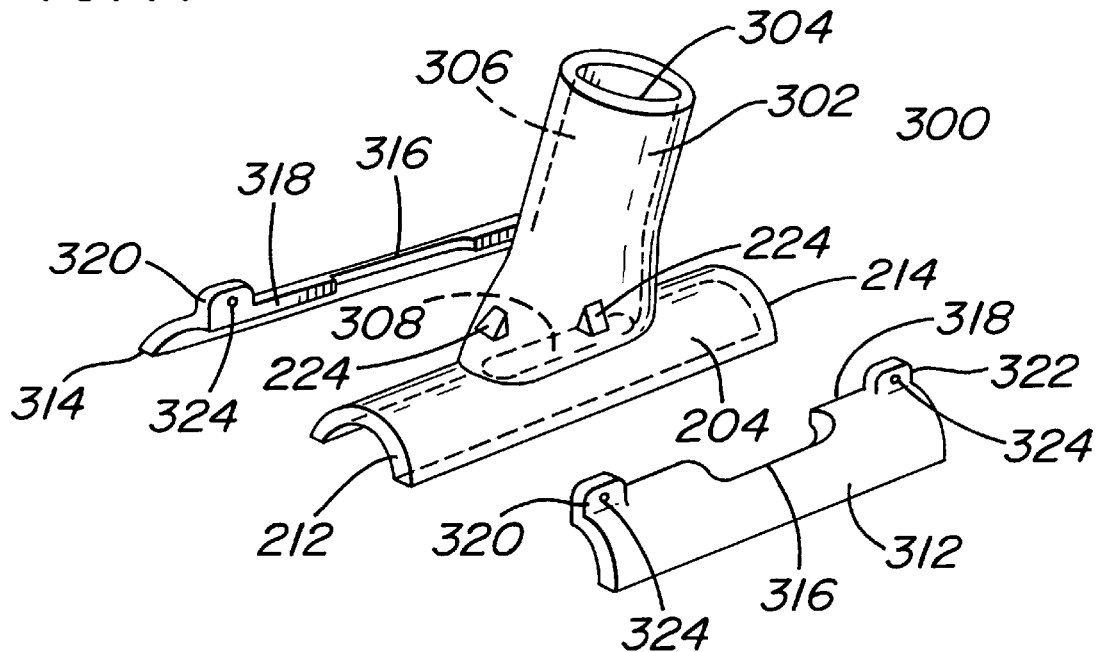
FIG. 17 is a slightly reduced exploded isometric view of the anastomosis device of FIG. 16.

In FIG. 16 there is shown an alternative embodiment 300 to the anastomosis connector 200 of FIGS. 14 and 15. The connector 300 is similar to the connector 200 except for the construction of its tubular portion and its locking plate. In particular, in embodiment 300 shown in FIGS. 16 and 17 the proximal portion 302 of the anastomosis connector device 300 is of a compound shape to accommodate a compound-shaped central passageway 304 therethrough. That passageway comprises a proximal end of circular cross-section 306 and a distal end 308 of a flattened oval cross-section. The cross-sectional area of the passageway from the circular end to the flattened oval end decreases in a controlled manner, either linearly or non-linearly, so that blood flowing therethrough from the larger diameter bypass graft to the smaller diameter native vessel is non-turbulent. The wall thickness of the extending tubular portion 302 is constant. Thus, the cross-sectional profile of the outer periphery of the extending portion of the connector 300 changes from circular to flat oval from the proximal end to the distal end where that portion merges with the culvert-shaped member 204.

The anastomosis device 300 also makes use of a locking plate 310, to be described hereinafter, and associated ramp-like detents 224 (constructed as described heretofore with reference to connector 200). However, due to the shape of the tubular extending portion 302 of the anastomosis connector, the locking plate 310 is not constructed like the unitary locking plate 220 of FIG. 14. Instead the locking plate 310 is formed as a two-piece unit of members 312 and 314. Each member is of an arcuate wall shape having an elongated rectangular, curved-corner recess 316 in one of its longitudinal marginal edges 318. Upstanding from the marginal edge 318 at each end thereof are respective tabs 320 and 322. Each tab includes an aperture 324 therein. The tabs 320 and 322 of the member 312 are arranged to abut the tabs 320 and 322, respectively, of the other member 314 to form a culvert-shaped cover plate having a rectangular, rounded corner shaped opening formed by the conjoining recesses 316. The two members are arranged to be secured together via respective sutures extended through their aligned apertures 324 as will be described hereinafter.

Use of the anastomosis connector 300 is as follows: The anastomosis connector 300 is introduced into the opening in the native vessel in the same manner as described with reference to the embodiment of connector 200 of FIG. 14. Once the culvert-shaped member 204 is located within the interior of the native vessel 10 such that its distal portion is located under the tissue contiguous with the distal end of the opening or slit 16 and its proximal portion is located under the tissue contiguous with the proximal or trailing end of the opening or slit 16 and with the tubular proximal portion 306 extending through the opening or slit 16, the locking plate elements 312 and 314 are brought together to form the locking plate 310. In particular, the two arcuate members 312 and 314 are brought together on the outer surface of the native vessel 10 so that their recesses 316 conjoin to form the central opening through which the tubular proximal portion 302 of the anastomosis connector 30 extends as shown in FIG. 16. The two members 312 and 314 are constructed so that the edges of their conjoining recesses 316 fit under the detents 224, thereby holding the two members closely against the outer surface of the native vessel 10. This action results in the alignment of the tabs 320 and 322 with each other so that their openings 324 align. A loop of suture material 326 can be then extended through each of the aligned openings 224 and knotted as shown in FIG. 16, thereby securing the two numbers 312 and 314 together. Accordingly, the two members now form a common locking plate 310 which is disposed over the interiorly located culvert-shaped member 204 so as to trap the contiguous portions of the wall of the native vessel therebetween.

As in the other embodiments described heretofore, the extending proximal end 302 of the anastomosis connector 300 includes the heretofore described means for securing it to the distal end of the bypass graft 12. Moreover the members making up the connector 300 and its locking plate are of the same composition as that described heretofore.

Figure 18:
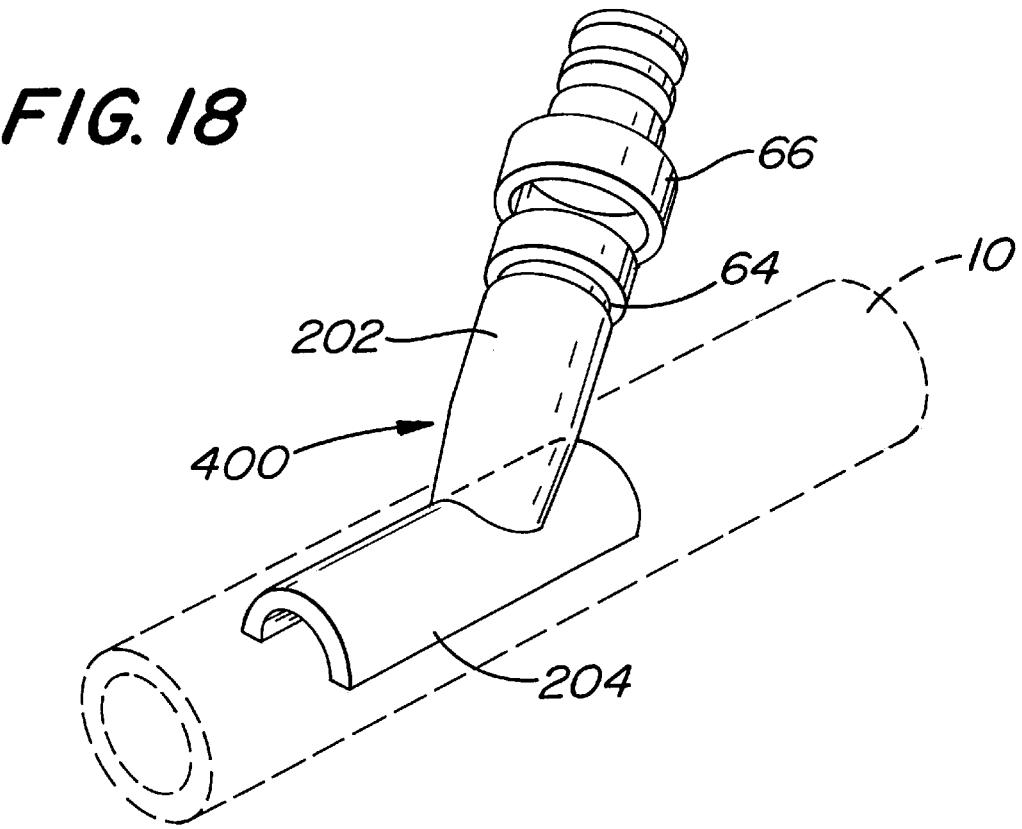
FIG. 18 is an isometric view showing the anastomosis device of FIG. 14 but utilizing an alternative means for securing the bypass graft thereto, i.e., a quick or snap-connector.

In FIG. 18 there is shown another alternative embodiment 400 of the anastomosis connector 200 shown in FIGS. 14 and 15. The anastomosis connector 400 is identical to connector 200 except for the means for connecting it to the bypass graft. In this regard, the connector 400 includes an annular recess 64 for snap-connection to a coupling 66 secured to the distal end 14 of the bypass graft 12.

Figure 19:
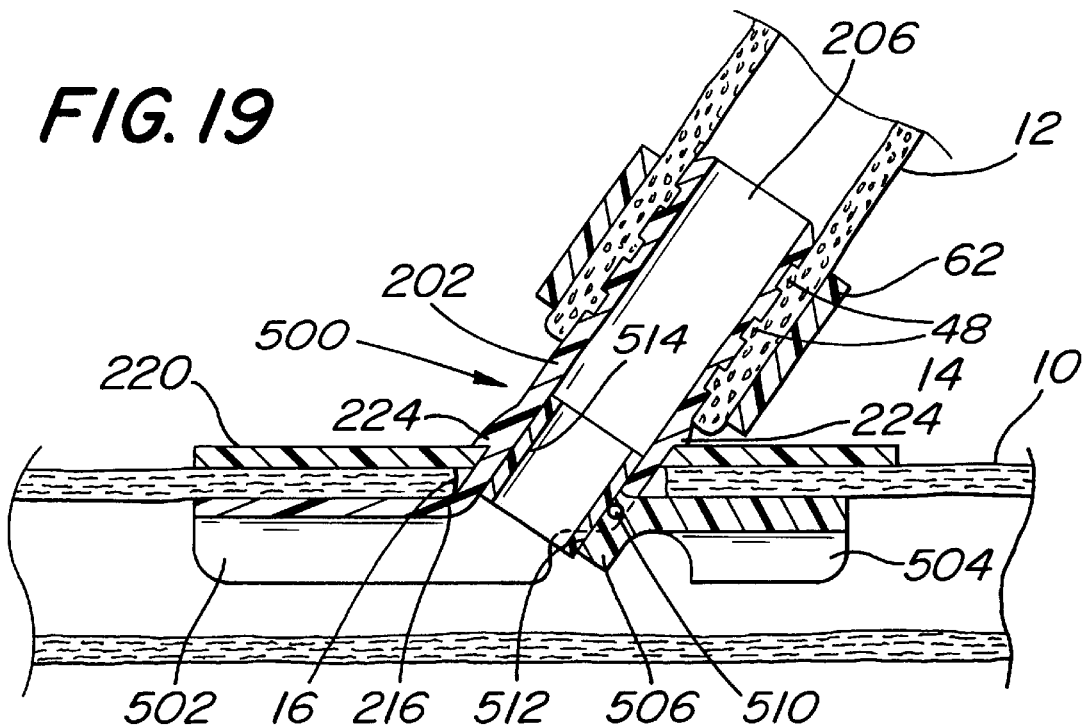
FIG. 19 is a sectional side elevational view like that of FIG. 14 but showing yet another alternative embodiment i.e., an extendable embodiment of the anastomosis device of this invention and which can be placed in position through a smaller opening in the native vessel.

In FIG. 19 there is shown another alternative embodiment 500 of the anastomosis connector 200 as shown in FIG. 14. The connector 500 is identical in all respects to the connector 200 except that its culvert-shaped member includes a retractable-extendable portion, to be described hereinafter, and a locking ring, also to be described hereinafter, to hold the member in an extended portion. The extendable/retractable portion of the culvert-shaped member, enables the connector 400 to be inserted through a shorter length slit or opening 16A in the native blood vessel 10 than the anastomosis connector 200 of FIG. 14.

Figure 20:
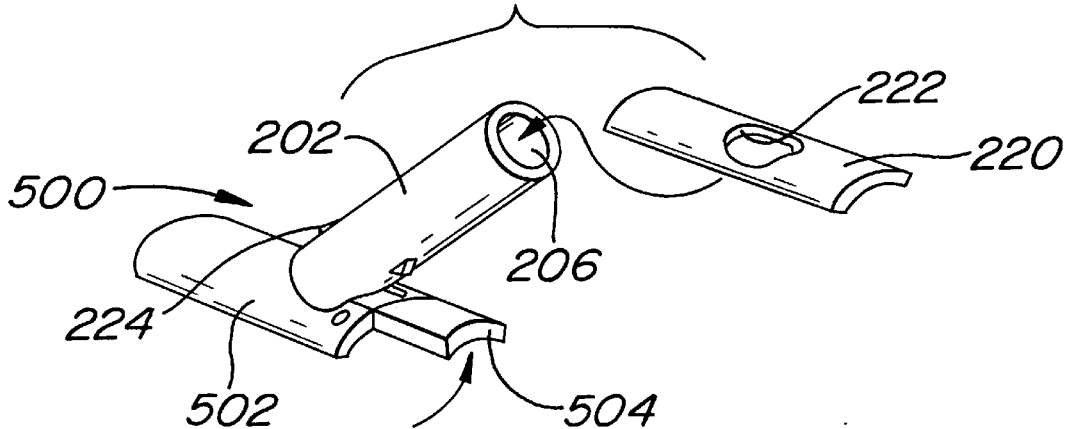
FIG. 20 is a reduced, exploded, isometric view showing the anastomosis device of FIG. 19.
Figure 21:
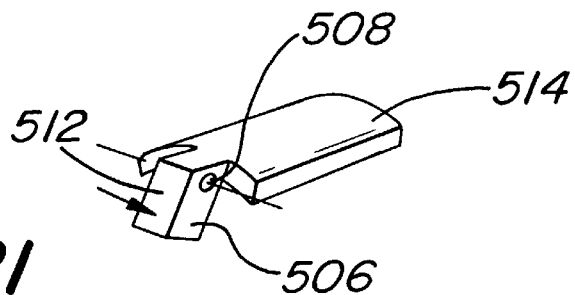
FIG. 21 is an enlarged, isometric view of a portion of the anastomosis device shown in FIGS. 19 and 20.

As can be seen in FIG. 19, in the exploded isometric view of FIG. 20, and in the isometric view of FIG. 21, the anastomosis connector 500 basically comprises a tubular proximal portion 202 (like that described earlier) and a culvert-shaped member 502. The culvert-shaped member 502 is constructed like the distal end portion 212 of the culvert-shaped member 204 of the connector 200 of FIG. 14. That is, it is fixedly secured to the tubular portion 202 of the connector at the distal end thereof. Unlike the embodiment of FIGS. 14 and 15, there is no rear fixed culvert-shaped portion 214. Instead an extendable culvert-shaped finger 504 is pivotally mounted onto the distal end of the tubular portion 202 opposite the fixed culvert-shaped portion 212. The extendable finger 504 is arranged to be pivoted from a retracted position, wherein it underlies the front culvert-shaped portion 502, to an extended position shown in FIG. 19, wherein it extends backward and opposite to the front culvert-shaped portion 502. The pivotable culvert-shaped finger 504 is of slightly arcuate shape in cross-section and includes a tab 506 projecting from its forward end. A transverse hole 508 (FIG. 21) is provided in the tab 506 through which a pivot pin 510 (FIG. 19) extends to pivotally mount the extendable finger 504 to the distal end of the tubular portion 202 at the rear of the front culvert-shaped portion 502. The tab 506 includes a stop surface 512 which extends at an acute angle to the longitudinal axis of the pivotable culvert-shaped finger 504.

Use of the anastomosis connector 500 of FIGS. 19 and 21 is as follows: The anastomosis connector with its extendable culvert-shaped finger in a retracted position, (that is, nested under the front culvert portion 502) and without the locking plate nor the bypass graft 12 secured thereto, is introduced into the interior of the native vessel 10 through its opening of slit 16A. In particular, the forward culvert-shaped portion 502 is extended through the slit 16A and slid distally so that the merger point 216 at which that member merges with the distal end of the tubular portion 202 abuts the leading end of the slit 16A as shown in FIG. 19. The trailing edge of the distal end 202 of the connector just clears the shorter length slit 16A so that the portion of the connector at which the extendable finger 504 is pivotally connected is also within the interior of the native vessel. The extendable culvert-shaped finger 504 can then be rotated from that retracted position to its extended position as shown in FIGS. 19 and 21 by introducing a suitable tool (not shown) through the passageway 206 in the tubular portion 202. The tool can then be used to press on the extending finger 502 to cause it to rotate in the counterclockwise direction as viewed in FIG. 19, until it is extended fully outward as shown in FIGS. 19 and 20. In this state the outer arcuate surface of the extendable culvert-shaped finger engages the inner surface of the native artery contiguous with the trailing edge of the slit 16A. A cylindrical locking ring 514 is then inserted through the central passageway 206 in the tubular portion 202 until it is at the position as shown in FIG. 19, whereupon its outer surface abuts the inclined stop surface 512 of tab of the extending finger 504. This action thereby locks the pivotable culvert-shaped finger in the extended position. The locking ring preferably is formed of the same resorbable material as the connector 500 and has a very thin sidewall so that it does not present any obstacle or impediment to the flow of blood through the connector's passageway 206, nor to create any blood turbulence therethrough.

Once the anastomosis connector 500 has been positioned so that the extending finger is locked in the extended position shown in FIG. 19 the locking plate 220 can then be slid down over the tubular portion 202 and over the inclined detent 224 as described with reference to connector 200. The distal end 14 of the bypass graft 12 can then be secured to the proximal end of the tubular portion 202 as described earlier, e.g., by use of the locking ring 62 or the encircling lashes 44.

In FIG. 20 there is shown an alternative embodiment 600 of an extendable anastomosis connector 500 of FIGS. 19–21. The alternative connector 600 and is identical in most respects to the anastomosis connector 100 shown in FIG. 12, except that it includes an extendable tubular intermediate end portion 602. That portion is arranged to be disposed totally within the connector 600 to facilitate the placement of the connector into an opening or slit 16A in the native artery 10 in a similar manner as just described with reference to the embodiment 500 of FIG. 19. In particular, the distal end 102 of the anastomosis connector 600 is introduced through the slit or opening 16A in the native artery wall and slid forward until the point as which it merges with the angular extending proximal tubular portion 104 abuts the leading edge of that slit. The extendable tubular member 602 is an elongated linear member formed of the same resorbable material as the connector 600 and is of an outside diameter just slightly less than the inside diameter of aligned passageways 110 and 112. It is initially disposed fully retracted within the connector 600, i.e., is in the position shown by the phantom lines in FIG. 22. Once the distal end portion 102 of the anastomosis connector 600 is located within the interior of the native vessel 10 the connector 600 can be pivoted downward to bring the rear edge its intermediate end portion 106 into the interior of the native vessel. As this time a tool (not shown) can be introduced through the passageway 108 in the proximal portion 104 of the connector to move the extendable tubular member 602 from its retracted position (shown by the phantom lines in FIG. 20) to the extended position shown in full therein.

The extendable tubular portion 602 includes a pair of annular recesses 48 about its free end. These recesses serve the same function as described earlier. Moreover the free end of the extendable member 602 is chamfered at 42 to facilitate its extension into the native vessel. Either the locking bands 62 or encircling lashes 44 can be used to secure the connector to the native vessel and bypass graft in the same manner as described earlier.

Figure 22:
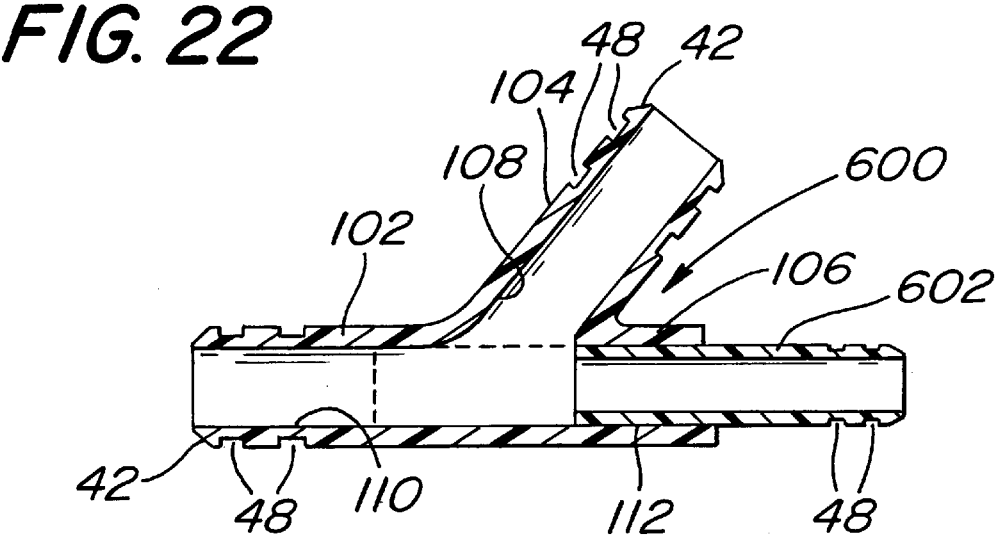
FIG. 22 is a longitudinal cross-sectional view of another alternative extendable anastomosis device of the subject invention for use in applications like that shown in FIG. 19.

It should be pointed out at this juncture that while not shown in FIG. 22, the passageway which extends through the angularly oriented tubular proximal portion 104 is also preferably of controlled decreasing diameter to minimize the occurrence of blood turbulence therethrough.

Figure 23:
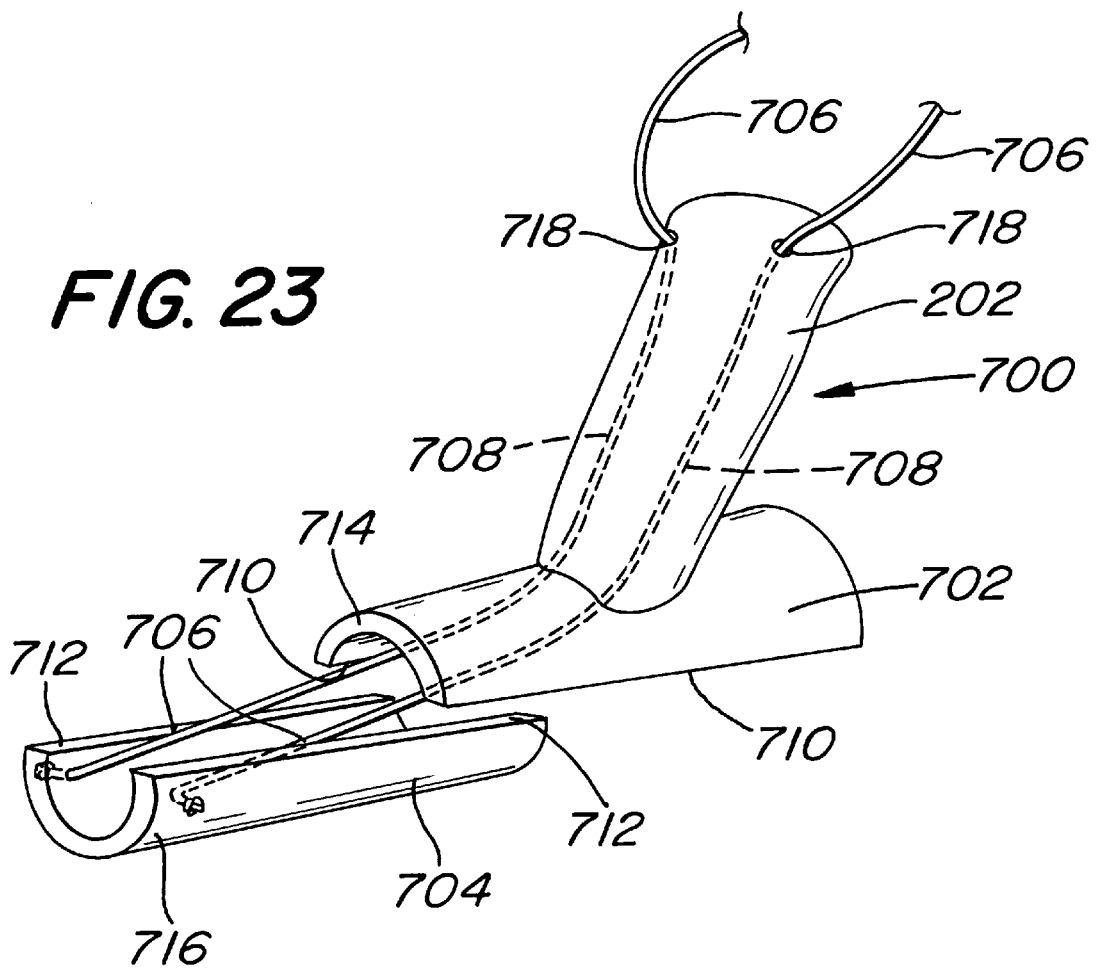
FIG. 23 is an isometric view of yet another alternative extendable anastomosis device of the subject invention for use in applications like that of FIGS. 19 and 22.

In FIG. 23 there is shown yet another alternative embodiment of an extendable anastomosis connector 700 constructed in accordance with this invention. That connector is also formed of a resorbable material and is similarly constructed to the anastomosis connector shown in FIG. 14. However, the anastomosis connector 700 of FIG. 23 includes a modified culvert-shaped portion 702, an extendable-retractable culvert-shaped member 704 and retraction filaments 706 therefore. The retraction filaments 706 extend under the culvert-shaped portion 702 and up through the central passageway in the connector portion 202, from whence they exit adjacent the proximal end thereof via a pair of ports or outlets 718. The modified culvert-shaped member 702 is fixedly secured to the tubular portion 202 and includes a pair of lower edges which do not extend parallel to the longitudinal axis of the culvert-shaped portion as is the case of the connector 200 shown in FIG. 14. Instead, the lower edges of the arcuate wall forming the modified culvert-shaped member 702 are each in the form of an inclined ramp surface 710 from the front edge to the rear edge. The extendable-retractable culvert-shaped member 704 basically comprises an arcuate or trough-shaped wall having a pair of upper edges 712 which slope from the front to the rear at the same angle as the surfaces 710 of the fixed culvert-shaped portion. T h e extendable-retractable culvert-shaped member 702 is arranged to be located distally of the distal end portion 714 of the fixed culvert-shaped member 702 and held in place by means (not shown) so that it is in approximately the position shown in FIG. 23 for introduction into the native vessel. The retraction filaments are in the form of flexible sutures which are connected to the distal end 116 of the movable culvert-shaped member 704 at portions immediately adjacent the sloped surface 712. Each suture extends backward from the extendable-retractable culvert-shaped member 704 under the distal portion of the fixed culvert-shaped member 702 and through the central passageway in portion 202 and out the outlets 718.

Use of the anastomosis connector 700 is as follows. The extendable-retractable culvert-shaped member 704 is first inserted into the interior of the native artery through the opening or slit in the wall therein by extending its leading end through that opening. The fixed culvert-shaped member 702 is then inserted through the opening in the same manner as described with reference to anastomosis connector 200. The two retraction filaments 706 are then pulled in the proximal direction by portions thereof which are located proximally of the outlets 718, thereby causing the retractable culvert-shaped member 704 to slide rearwardly in the native blood vessel 10 toward fixed culvert-shaped member 702. In particular, the sloped surface is 712 of the extendable-retractable (movable) culvert-shaped member 704 engage the ramp surfaces 710 of the fixed culvert-shaped member 702 and slide therealong. When the movable culvert-shaped member 704 is fully retracted with respect to the fixed culvert-shaped member 702, that is its leading edge is contiguous with the leading edge of the fixed culvert-shaped member and its trailing edge is contiguous with the trailing edge thereof, the two arcuate culvert-shaped members 702 and 704 conjoin to form a circular, tubular member which acts to support the entire periphery of the native artery thereabout. This action will prevent the accidental removal of the anastomosis connector 700, i.e., it locks the connector in place. If desired the anastomosis connector 700 can also include a locking plate 220 and associated detents 224 like that described heretofore. While not shown in FIG. 21 the anastomosis connector also includes any of the means as described heretofore for effecting the securement of the distal end of the bypass graft 12 thereto.

In FIGS. 24–30 there is shown yet other embodiments of an extendable anastomosis connector 800 constructed in accordance with this invention. The connector 800 shown in FIG. 24 is basically the same as connector device 200 except that it includes an evertable member 802 secured to the culvert-shaped member 204. The evertable member 802 preferably comprises a mesh which is connected to the culvert-shaped member 204 adjacent each of its bottom edges. The mesh 802 is arranged to be everted by a tool (not shown) extended through the passageway in tubular portion 202 so that it everts from the retracted position shown in FIG. 28 to the everted position shown in FIGS. 24 and 25. In FIGS. 29 and 30 the evertable member 802 are shown in successive stages of eversion. In its fully everted position shown in FIGS. 24 and 25 the mesh 802 and the culvert-shaped member 204 together define a cylindrical tube for supporting the entire periphery of the native vessel contiguous with the opening therein in the same manner as described with reference to the connector 700.

The mesh forming the evertable member 802 may alternatively be initially disposed so that it lies in a plane extending between the two bottom edges of the fixed culvert-shaped member as shown in FIGS. 26 and 27.

It should be pointed out that the evertable member 802 of the connector device 800 need not be a mesh, but can be of any type construction so that it can be moved or everted to an extended position wherein it engages and supports the periphery of the native vessel thereon.

If desired, the anastomosis connector 800 of FIG. 24 can include the locking plate and inclined detents as described earlier. Moreover, it may include any of the means as described earlier for holding it in place, e.g., the use of the annular recesses and associated rings, lashes, etc.

Figure 31:
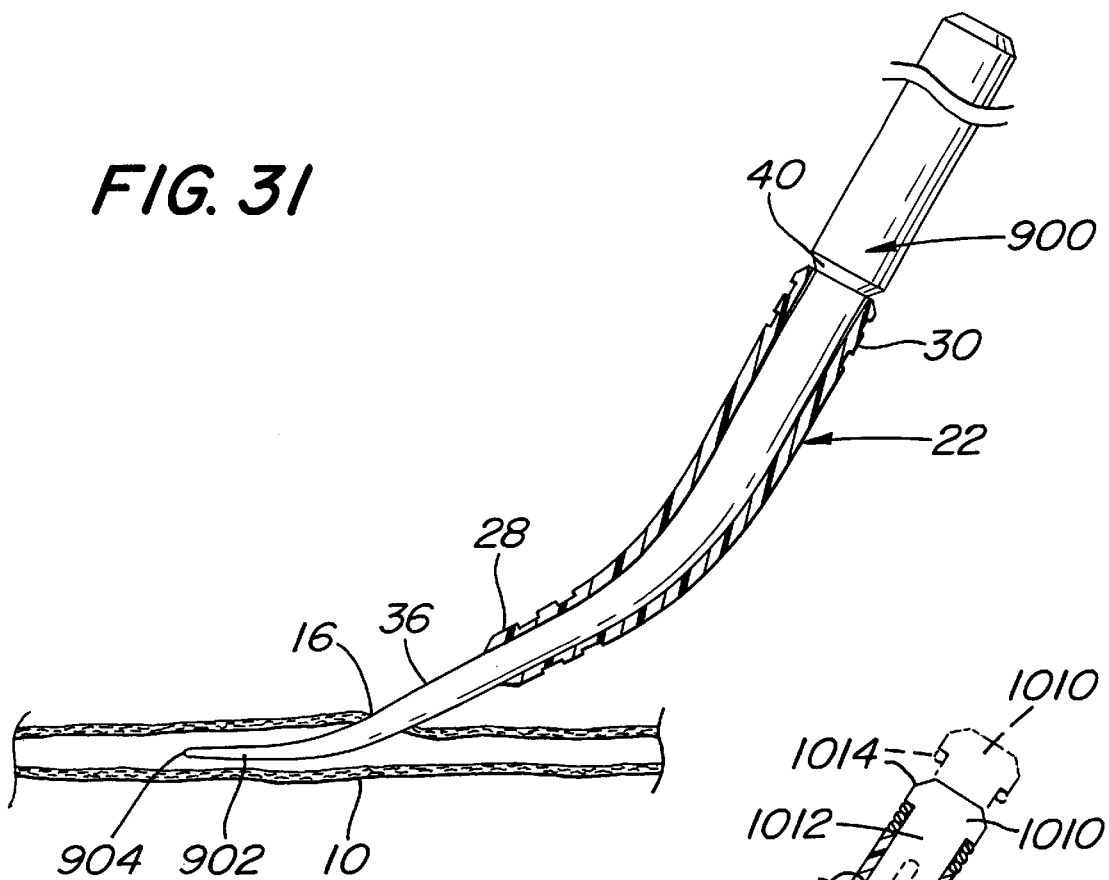
FIG. 31 is a view similar to FIG. 2, but showing an alternative embodiment of a deployment instrument constructed in accordance with this invention.

In FIG. 31 there is shown an alternative embodiment of a deployment instrument 900 constructed in accordance with this invention. The instrument 900 is identical to the instrument 24 except that it includes a distal end portion 902 which may obviate the need for a guide to place the instrument with the anastomosis connector device 22 therein into the native vessel 10 through the opening or slit 16. In the interest of brevity the common components of the instruments 900 and 24 will be given the same reference numbers and their description will not be reiterated. The proximal end of the dilator tip 36 is in the form of an elongated, flexible extension 902. The extension can be slightly tapered or may be of constant diameter similar to that of the guide wire 26. The extension is preferably form of a material having a softer durometer than that of the dilating portion of the instrument. The intermediate portion of the instrument 900 extending proximally from the dilating surface 36 may be of constant diameter up to the shoulder 40 or may flare slightly, as shown in FIG. 31, so that it fills the central passageway 32 in the anastomosis connector device 22. In any case, use of the instrument 900 is similar to that of instrument 24, except that the free end 904 of the flexible tip 902 is first inserted into the opening or slit 16 in the native vessel and then the instrument pushed therein so that the tip 902 guides the instrument therein. The flared dilation surface 36 of the instrument engages the tissue of the native vessel 10 contiguous with the opening or slit 16 to dilate it slightly and allow the instrument 900 to pass therethrough carrying the anastomosis connector device 22 with it, as described earlier.

Figure 32:
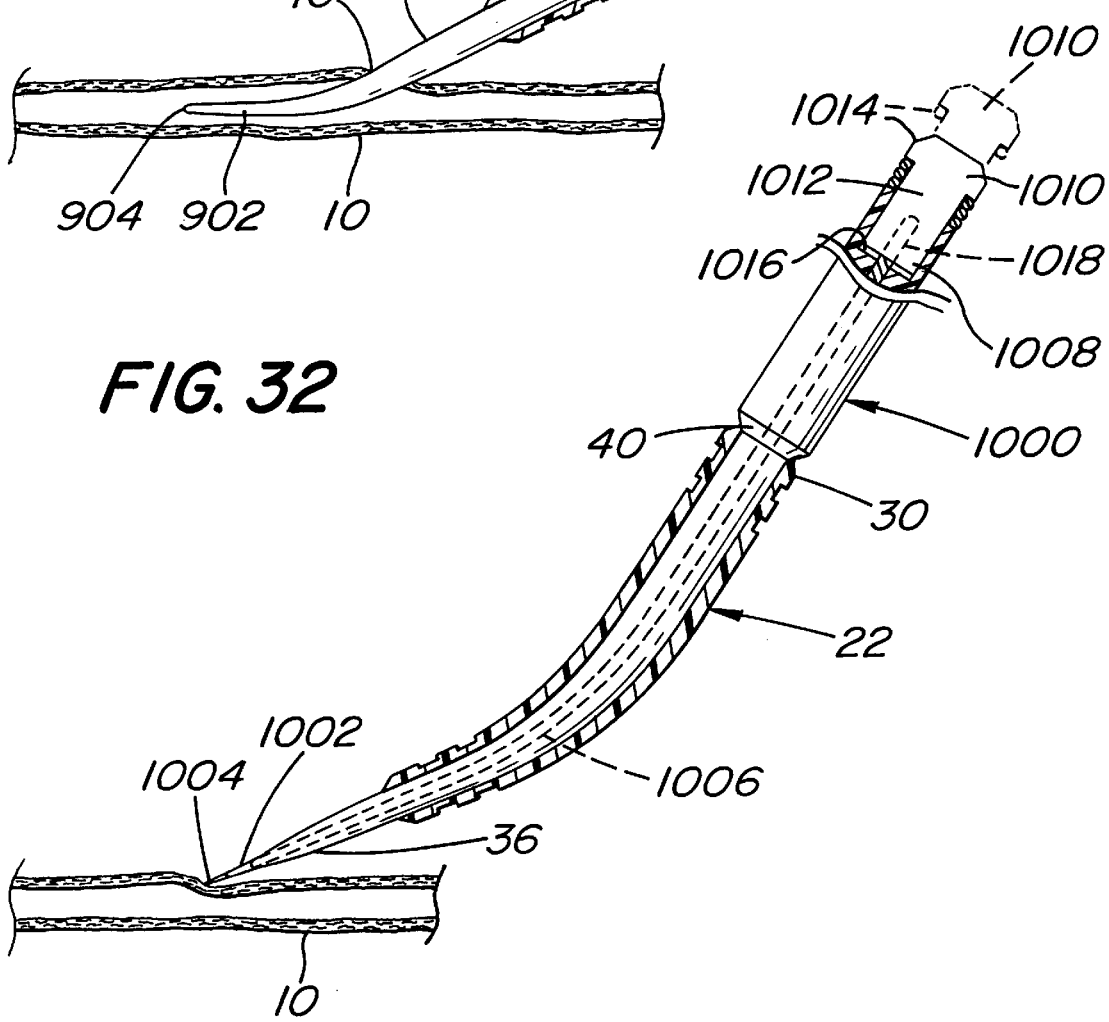
FIG. 32 is a view similar to FIG. 2, but showing yet another alternative embodiment of a deployment instrument constructed in accordance with this invention.

In FIG. 32 there is shown another alternative embodiment of a deployment instrument 1000 constructed in accordance with this invention. The instrument 1000 is similar to the instrument 24. Thus, its common components will be given the same reference numbers as those of instrument 24. Unlike instrument 24, the instrument 1000 it is arranged to puncture the wall of the native vessel 10 to form the opening or slit into which the anastomosis connector 22 will be placed by the instrument. To that end, the instrument 1000 includes an extendable flexible central member 1002 having a free distal end in the form of a piercing point 1004. The piercing point 1004 may gradually taper to a point (as shown) or may be of constant outside diameter and include a sharply chiseled end surface. In any case, the extendable central member 1002 extends through a central lumen or passageway 1006 in the deployment instrument 1000 and terminates at a proximal end fixedly secured to a plunger member 1008. The plunger member 1008 is a cylindrical member having an enlarged diameter head or cap 1010 and a smaller diameter forward section 1012. A helical compression spring 1014 is disposed about the section 1012. The forward section 1012 of the plunger member is located within a matingly shaped bore 1016 at the proximal end of the instrument 1000. The spring 1014 is interposed between the head or cap 1010 of the plunger and the proximal end of the instrument 1000. The proximal end 1018 of the extendable central member 1002 is fixedly secured within a central bore in the distal end of the plunger 1008.

Use of the instrument is as follows. The instrument 1000 with the anastomosis connector 22 thereon is positioned so that the dilating surface 36 of the instrument is adjacent the situs of the native blood vessel where the opening or slit 16 is to be formed. At this time no force is applied to the head or cap 1010 of the plunger 1008, so that the spring 1014 biases the plunger to the retracted position shown by the phantom lines in FIG. 32. When the distal end of the instrument is at the desired location the plunger cap or head 1010 is pressed to move it in the distal direction with respect to the instrument 1000, whereupon the piercing tip 1004 of the instrument is extended out of the instrument and into engagement with the wall of the native vessel 10 as shown in FIG. 32. The instrument is then pushed toward the native blood vessel to cause the tip 1004 to pierce or puncture the wall of the native blood vessel and thereby form the opening or slit 16. The instrument 1000 can then be pushed further into the opening or slit to cause its dilating surface 36 to dilate that opening or slit, as described earlier. The plunger may be released at this time so that the spring 1014 carries the plunger and extendable member 1002 proximally, thereby retracting the piercing tip 1004 within the instrument. This action insures that the piercing tip will not damage the interior of the native vessel as the instrument is pushed therein to carry the anastomosis device 22 into position. In particular, the instrument 1001 is pushed further into the opening or slit to carry the anastomosis connector device 22 therein, as described earlier.

It should be pointed out at this juncture that the various features of any of the embodiments of the anastomosis connector device and/or its deployment instrument as disclosed herein can be used in any of the other embodiments. Thus, the embodiments as shown and described heretofore are merely exemplary. Moreover, the anastomosis connector devices need not be formed to be totally resorbable. Thus, only portions thereof may be resorbable. Also the deployment instrument may be formed of resorbable portions to enable it to be left within the patient's body after placement of the anastomosis connector.

Without further elaboration the foregoing will so fully illustrate our invention that others may, by applying current or future knowledge, adopt the same for use under various conditions of service.

We claim:

1. An anastomosis connection system for facilitating a bypass of a native blood vessel in a living being with a bypass graft, the native blood vessel having a wall with an opening provided therein, said anastomosis system comprising a deployment instrument, an anastomosis connector, and securement means, said anastomosis connector being a tubular member having a first portion and a second portion and a passageway extending therebetween, at least a portion of said anastomosis connector being resorbable, said deployment instrument having a distal portion for carrying said first portion of said anastomosis connector through the opening in the wall of the native blood vessel for location within the native blood vessel so that said second portion of said anastomosis connector is located outside of the native blood vessel, said securement means being arranged to secure said anastomosis connector to the native blood vessel, said second portion of said anastomosis connector being arranged for connecting the bypass graft thereto, whereupon blood is enabled to flow between said native blood vessel and said bypass graft through said passageway in said anastomosis connector.

2. The anastomosis connection system of claim 1 wherein said securement means is arranged to be applied outside of the native blood vessel to secure said anastomosis connector to the native blood vessel.

3. The anastomosis connection system of claim 2 wherein said securement means is arranged to encircle a portion of the native blood vessel.

4. The anastomosis connection system of claim 3 wherein said securement means comprises a flexible filament.

5. The anastomosis connection system of claim 3 wherein said securement means comprises a preformed ring.

6. The anastomosis connection system of claim 1 wherein the bypass graft includes a distal end, and wherein said system additionally comprising a connector located on said distal end of the bypass graft and a cooperating connector located on said second portion of said anastomosis connector.

7. The anastomosis connection system of claim 6 wherein said connectors are arranged to snap-connect to each other.

8. The anastomosis connection system of claim 1 additionally comprising a guide member adapted to be introduced through a portion of the body of the being to a point within the native vessel located distally of the opening in the native blood vessel for guiding said deployment instrument with said anastomosis connector thereon to a desired position.

9. The anastomosis connection system of claim 8 wherein said guide member comprises an elongated guide wire.

10. The anastomosis connection system of claim 1 wherein said deployment instrument is arranged to stretch the native blood vessel contiguous with the opening therein to facilitate the introduction of the first portion of the anastomosis connector into the native blood vessel.

11. A method for bypassing a portion of a native blood vessel in a living being with a bypass vessel, the native vessel having a side wall portion, and the bypass vessel comprising a tubular member having an open distal end, said method comprising the steps of:

(A) forming an opening in the side wall portion of the native blood vessel, (B) providing an anastomosis connector having a first portion, a second portion and a passageway extending therebetween, at least a portion of said anastomosis connector being absorbable, (C) locating said anastomosis connector at an operative position wherein said first portion of said anastomosis connector is located within said native blood vessel distally of the opening therein and wherein said second portion of said anastomosis connector is located externally of the native blood vessel, (D) providing the bypass vessel, (E) securing a portion of the distal end of said bypass vessel to second portion of said anastomosis connector to connect the bypass vessel to the native blood vessel and enable blood to flow through said passageway between the native blood vessel and the bypass graft, (F) leaving said anastomosis connector in place, whereupon said at least one resorbable portion is resorbed.

12. The method of claim 11 wherein said native blood vessel comprises an artery.

13. The method of claim 11, wherein said anastomosis connector is carried into the body of the being by a deployment instrument.

14. The method of claim 13 additionally comprising the step of withdrawing said deployment instrument from the body of the being after the bypass vessel is secured to said native blood vessel.

15. The method of claim 13 additionally comprising the step of providing guiding means to guide the deployment instrument with said anastomosis device thereon to said operative position.

16. The method of claim 13 wherein said anastomosis connector is mounted on said deployment instrument outside the body of the being.

17. The method of claim 11 additionally comprising the step of suturing the bypass vessel to the native blood vessel.

18. The method of claim 11 additionally comprising the step of stretching the native blood vessel adjacent said opening to facilitate the introduction of said first portion of said anastomosis connector in the native blood vessel.

19. The method of claim 18, wherein said anastomosis connector is carried into the body of the being by a deployment instrument.

20. The method of claim 19 additionally comprising the step of stretching the native blood vessel adjacent said opening to facilitate the introduction of said first portion of said anastomosis connector in the native blood vessel.

21. The method of claim 20 wherein said deployment instrument is used to stretch the native blood vessel adjacent the opening.

22. The method of claim 11 additionally comprising the step of controlling the cross sectional area of said passageway in said anastomosis connector to reduce blood turbulence through said passageway.

23. The method of claim 11 additionally comprising the steps of securing the first portion of said anastomosis connector to said native blood vessel.

24. The method of claim 23 wherein said first portion of said anastomosis connector is secured to the native blood vessel by an externally applied securement member.

25. The method of claim 24 wherein said externally applied securement member comprises a filament.

26. The method of claim 24 wherein said externally applied securement member comprises a preformed ring.

27. The method of claim 11 wherein said second portion of said anastomosis connector is secured to the bypass vessel by a snap connector.

* * * * *